United States Patent [19]

Klemarczyk et al.

[11] 4,310,681

[45] Jan. 12, 1982

[54] CARBOALKOXY ALKYL NORBORNANE DERIVATIVES AND PROCESS FOR PREPARING SAME

[75] Inventors: Philip T. Klemarczyk, Old Bridge; James M. Sanders, Eatontown; Manfred H. Vock, Locust; Joaquin F. Vinals, Red Bank; Frederick L. Schmitt, Holmdel; Edward J. Granda, Englishtown, all of N.J.

[73] Assignee: International Flavors & Fragrances Inc., New York, N.Y.

[21] Appl. No.: 152,201

[22] Filed: May 22, 1980

Related U.S. Application Data

[63] Continuation-in-part of Ser. No. 133,870, Mar. 25, 1980.

[51] Int. Cl.³ .................... C07C 67/30; C07C 69/753
[52] U.S. Cl. ............................... 560/120; 131/300; 252/8.6; 252/174.11; 252/522 R; 424/127; 424/167; 426/534
[58] Field of Search ........................................ 560/120

[56] References Cited

U.S. PATENT DOCUMENTS

| | | | |
|---|---|---|---|
| 2,264,354 | 12/1941 | Alder et al. | 560/120 X |
| 2,688,021 | 8/1954 | Jenkins | 560/120 X |
| 3,225,084 | 12/1965 | Koch | 560/120 |

*Primary Examiner*—Natalie Trousof
*Assistant Examiner*—Vera C. Clarke
*Attorney, Agent, or Firm*—Arthur L. Liberman

[57] ABSTRACT

Described are compounds having the generic structure:

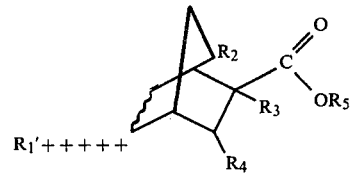

wherein each of the lines + + + + and the wavy line represent single or carbon-carbon double bonds; wherein each of $R_2$, $R_3$ and $R_4$ represents hydrogen or methyl and $R_1'$ represents hydrogen, methyl or methylene; wherein $R_5$ represents $C_1$–$C_4$ alkyl; with the proviso that when $R_2$ is $CH_3$, $R_1'$ is hydrogen and + + + + represents a single bond and the wavy line represents a carbon-carbon single bond or a carbon-carbon double bond; and with the further proviso that when $R_2$ is hydrogen, $R_1'$ is methyl and + + + + represents a carbon-carbon single bond and the wavy line represents a carbon-carbon double bond or a carbon-carbon single bond or $R_1'$ is methylene ($CH_2$) and + + + + is a carbon-carbon double bond and the wavy line is a carbon-carbon single bond are disclosed.

In addition, organoleptic uses of such compounds are disclosed for augmenting or enhancing the aroma or taste of consumable materials including foodstuffs, chewing gums, chewing tobaccos, medicinal products, toothpastes, perfumed articles (such as liquid or solid anionic, cationic, nonionic or zwitterionic detergents, fabric softeners, dryer added fabric softener articles and cosmetic compositions), perfumed compositions, smoking tobaccos and smoking tobacco articles. Also disclosed is a process for preparing such compounds using the reaction scheme or parts of said reaction scheme:

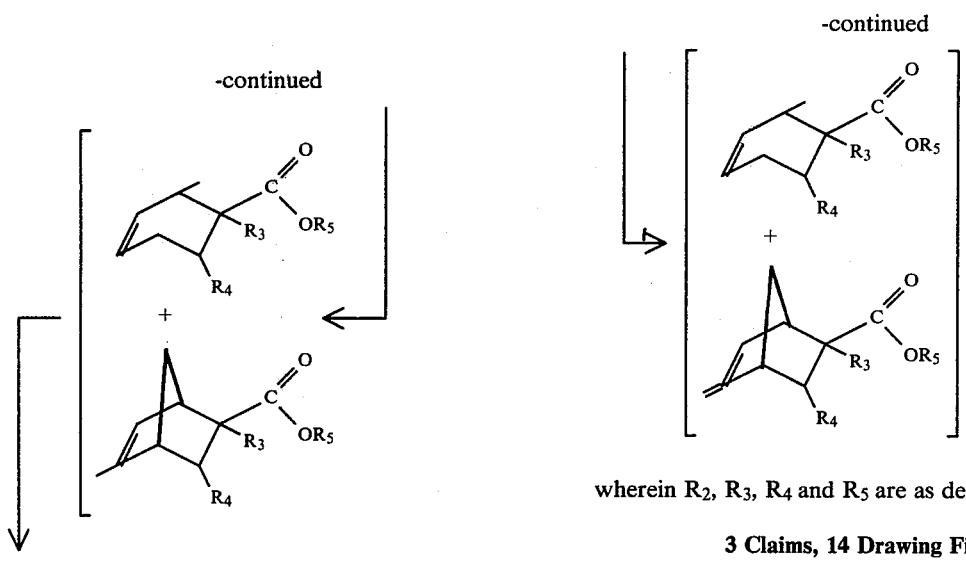
wherein $R_2$, $R_3$, $R_4$ and $R_5$ are as defined above.
3 Claims, 14 Drawing Figures

GLC PROFILE FOR EXAMPLE I. CRUDE WASHED BEFORE DISTILLATION.

GLC PROFILE FOR EXAMPLE I, BULKED FRACTIONS 7-12.

NMR SPECTRUM FOR EXAMPLE I.

NMR SPECTRUM FOR EXAMPLE I.

IR SPECTRUM FOR EXAMPLE I.

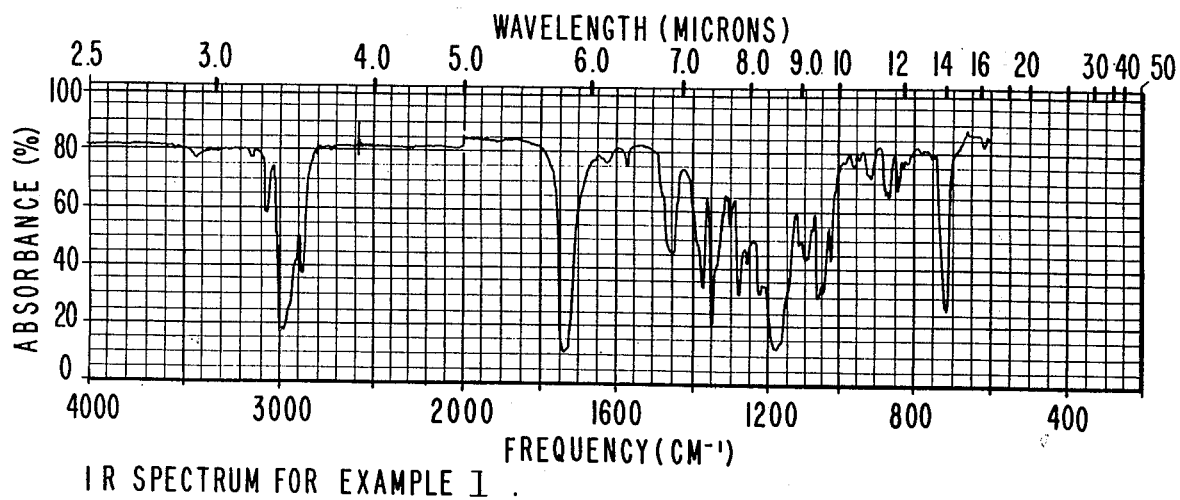
IR SPECTRUM FOR EXAMPLE 1.
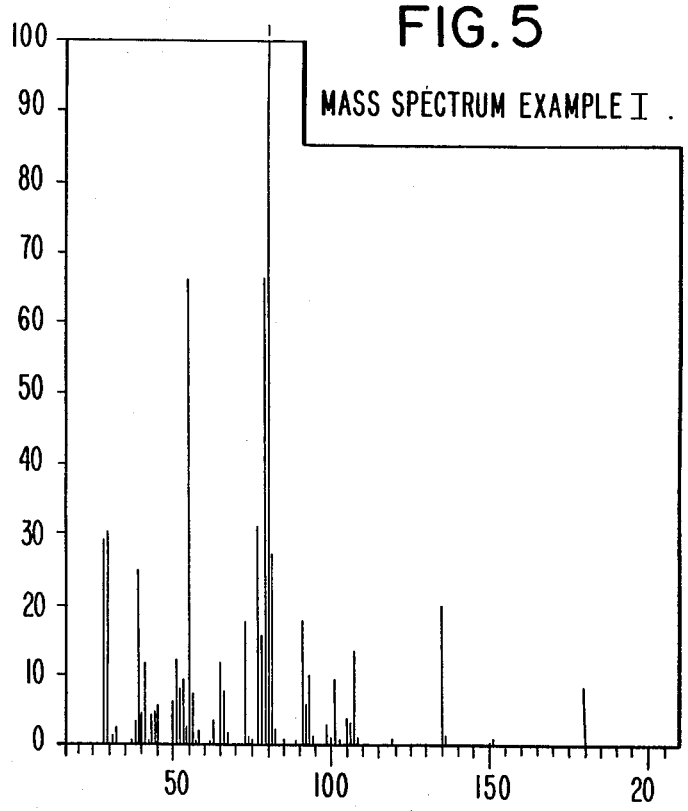
MASS SPECTRUM EXAMPLE 1.

GLC PROFILE FOR EXAMPLE II.

GLC PROFILE FOR EXAMPLE III.

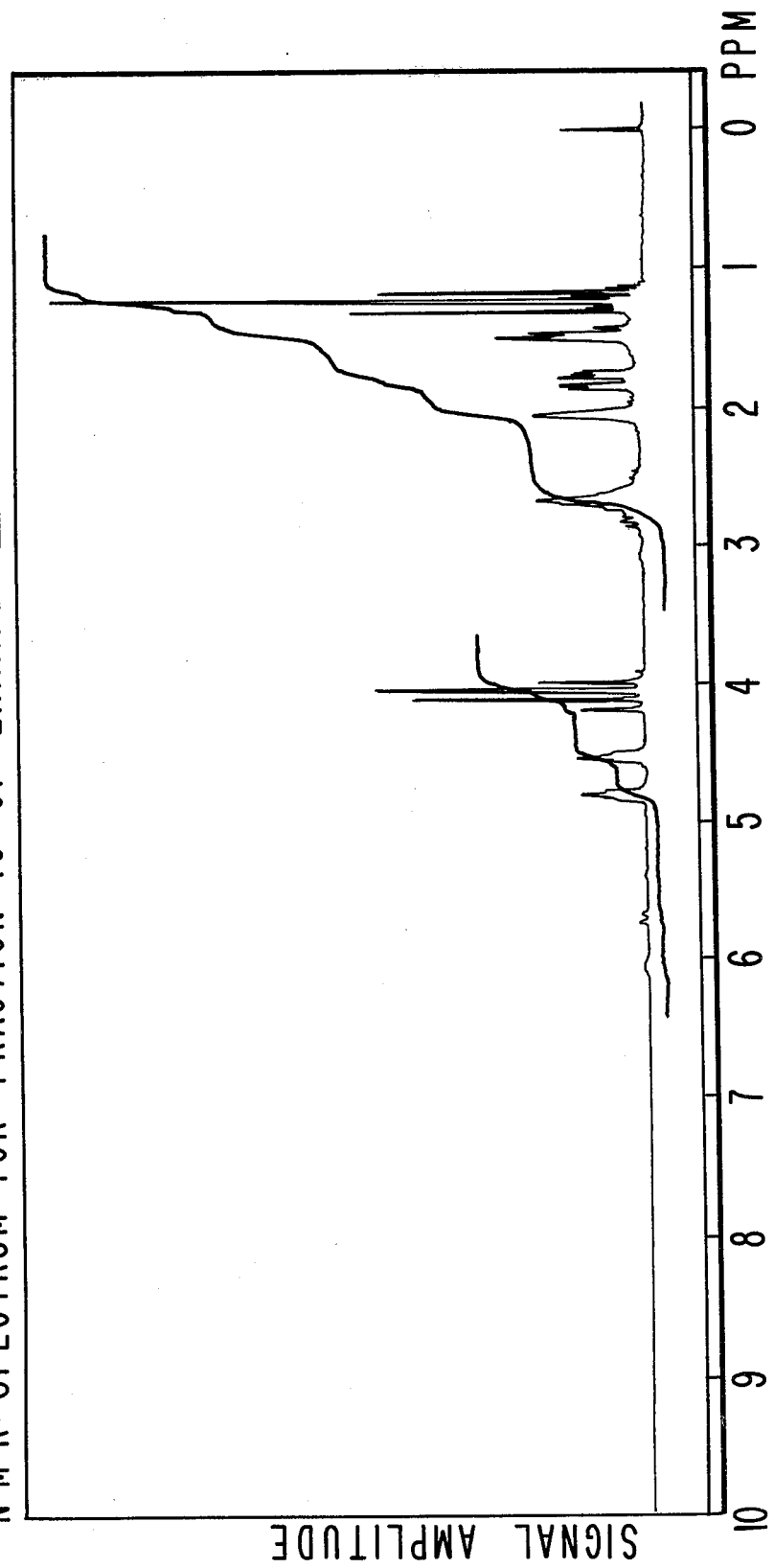

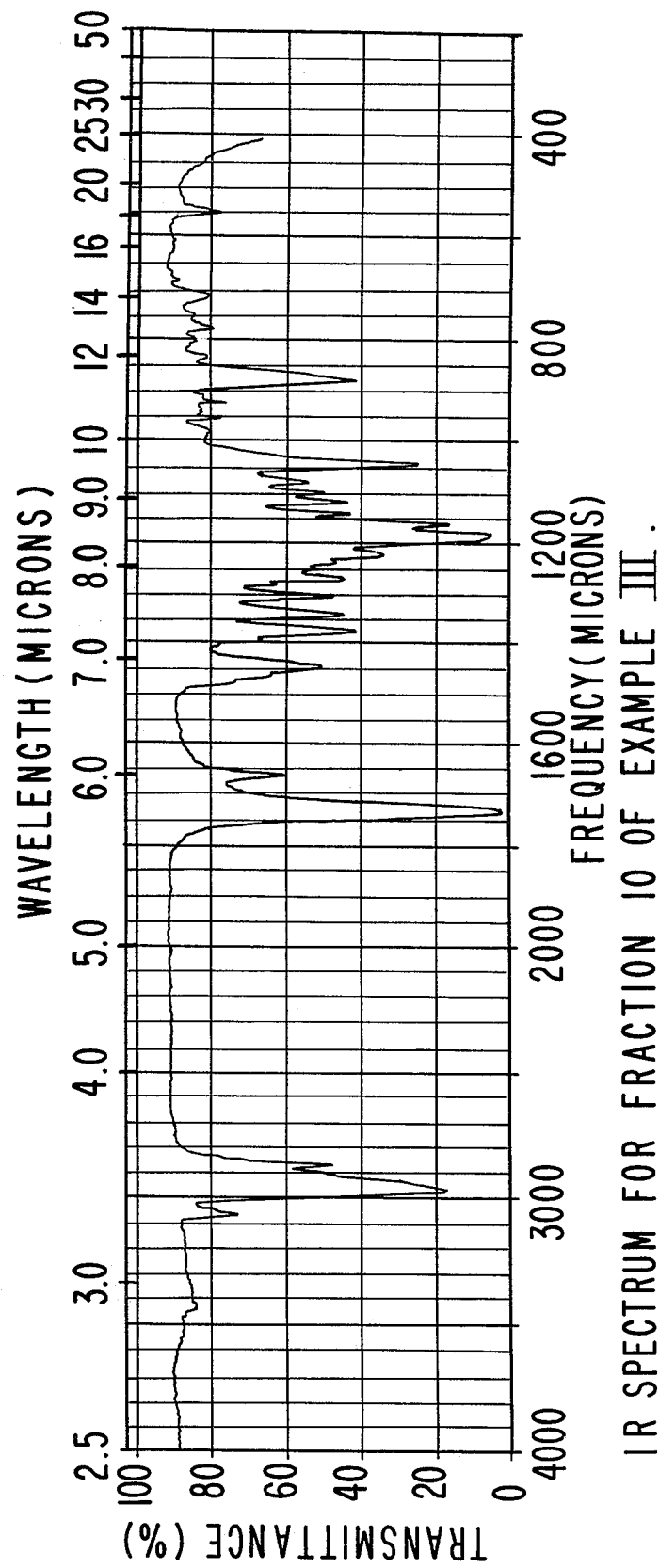

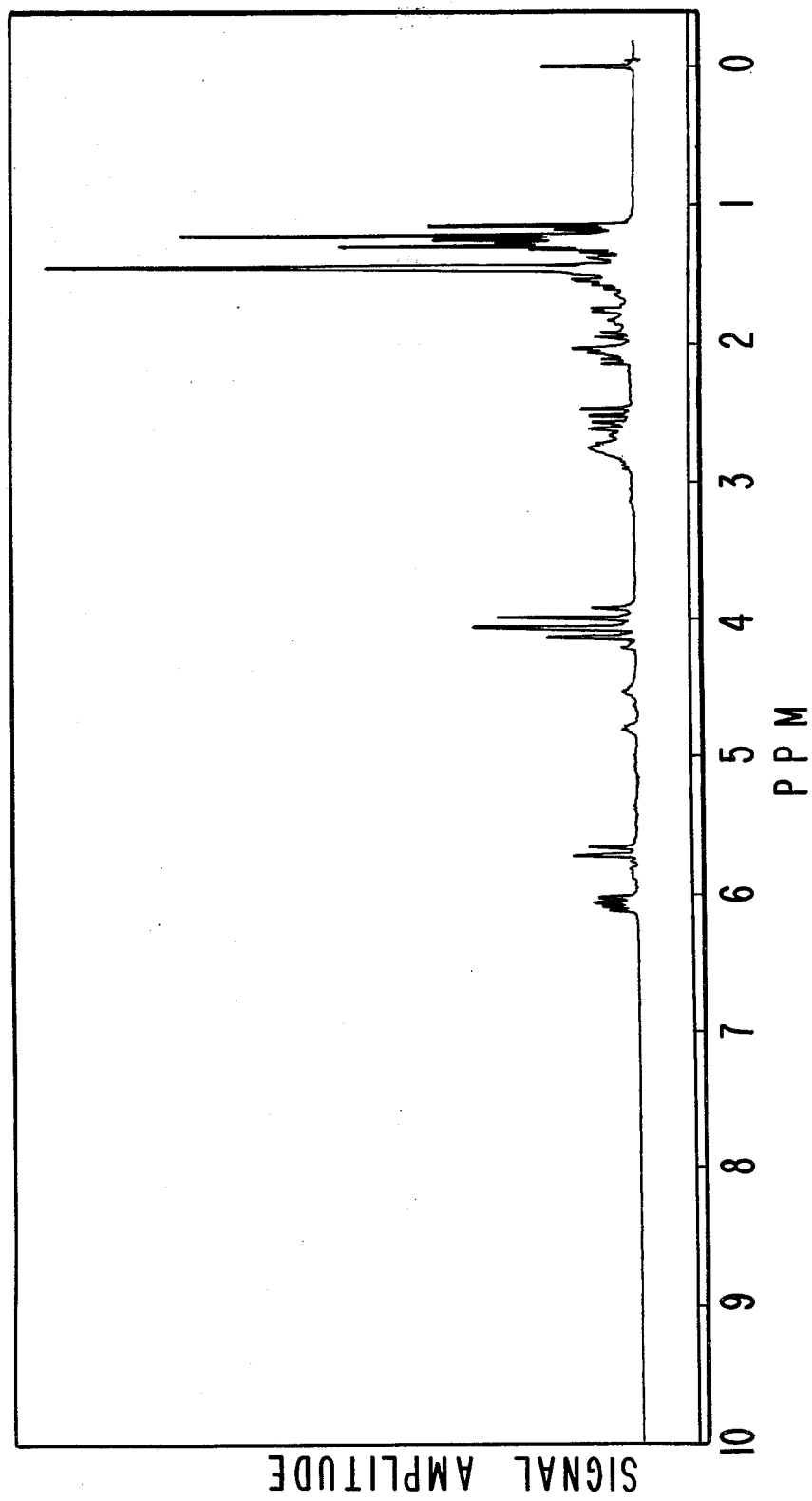

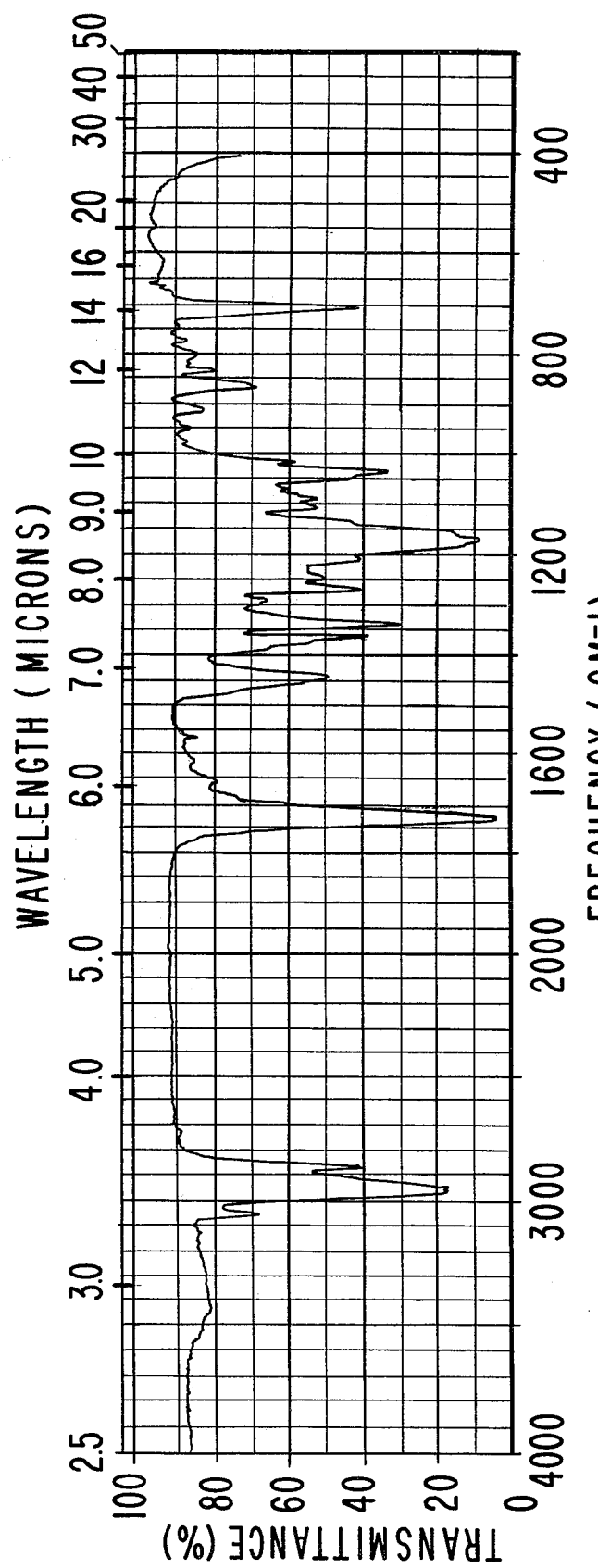

MASS SPECTRUM FOR EXAMPLE III.

CARBOALKOXY ALKYL NORBORNANE DERIVATIVES AND PROCESS FOR PREPARING SAME

This application is a continuation-in-part of Application for U.S. Ser. No. 133,870 filed on Mar. 25, 1980.

BACKGROUND OF THE INVENTION

The present invention relates to carboalkoxy alkyl norbornanes derivatives having the generic formula:

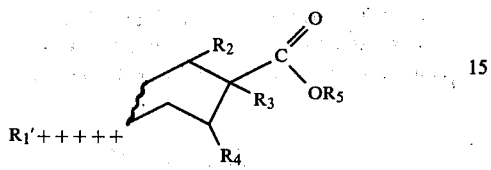

wherein each of the lines ++++ and the wavy line represent single or carbon-carbon double bonds; wherein each of $R_2$, $R_3$ and $R_4$ represents hydrogen or methyl and $R_1'$ represents hydrogen, methyl or methylene; wherein $R_5$ represents $C_1$-$C_4$ alkyl; with the proviso that when $R_2$ is $CH_3$, $R_1'$ is hydrogen and ++++ represents a single bond and the wavy line represents a carbon-carbon single bond or a carbon-carbon double bond; and with the further proviso that when $R_2$ is hydrogen, $R_1'$ is methyl and ++++ represents a carbon-carbon single bond and the wavy line represents a carbon-carbon double bond or a carbon-carbon single bond or $R_1'$ is methylene ($CH_2$) and ++++ is a carbon-carbon double bond and the wavy line is a carbon-carbon single bond produced by the novel process of our invention, and to novel compositions using one or more of such norbornane derivatives to alter, modify or augment or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Fruity, jasmine-like, burnt fruit-like, raspberry, sweet, green, seedy, berry-like, red berry-like, blueberry-like, spicy, black pepper-like, herbaceous, clove-like, vermouth-like, strawberry-like and balsamic aromas with fruity, jasmine-like, burnt fruit-like, raspberry, seedy, sweet, berry-like, red berry-like, blueberry-like, spicy, black pepper-like, green, herbaceous, clove-like, vermouth-like, strawberry-like, balsamic and bitter tastes are particularly desirable for many uses in foodstuff flavors, chewing gum flavors, toothpaste flavors and medicinal product flavors.

Spicy, cooling, clove-like, cinnamon bark-like, sweet, fruity, berry-like, juicyfruit, woody, piney, blueberry, banana, green, herbaceous, strawberry-like and dill aroma and taste characteristics both prior to and on smoking in the mainstream and in the side stream.

Intense, long lasting and pleasant fruity, banana-like, creamy, camphoraceous, herbaceous, sweet, spicy, woody, eucalyptol-like, rum/butterscotch-like, balsamic, green, minty, borneol-like and "medicinal" aromas with strong, chamomile-like, camphor, minty and calamnus-like undertones are desirable in several types of perfume compositions, perfumed articles and colognes.

Arctander, "Perfume and Flavor Chemicals" 1969, Volume I discloses the use in perfume compositions and in foodstuff flavors of camphene carbinyl acetate thus:

"1029: 2,2-Dimethyl-Delta-2-beta-norbornane-2-ethylacetate

"Camphene carbinyl acetate".

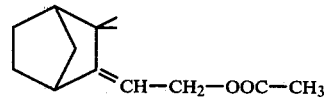

Mild and sweet-woody odor with a floral-piney undertone. The commercial products are probably not well defined single chemicals, and great variations in odor have been observed.

This ester has been developed in line with the research on Sandalwood type odors. The parent alcohol "Camphene carbinol" was once considered useful as a Sandalwood type material, but is has found more use as a sweetening and enriching ingredient in sophisticated pine fragrances. The title ester finds limited use in perfume compositions of woody character, Fougeres, Pine fragrances, etc. and it blends very well with the Cyclohexanol derivatives, Ionones, iso-Bornylacetate, Nitromusks, etc."

Meller and Webb, J. Chem. Soc. Perkin Trans II, 1974 (I) 26–31 discloses production of the compounds having the structures:

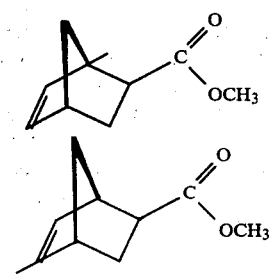

together with several other methyl substituted isomers thereof in admixture, according to the reaction:

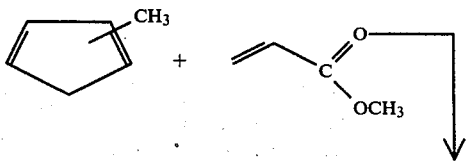

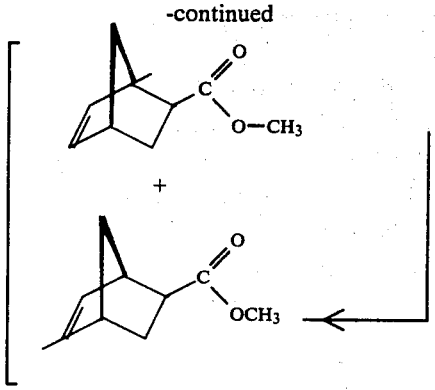

The Mellor and Webb article however, does not disclose the reaction to take place at low temperatures in the pressence of an alkyl aluminum halide or dialkyl aluminum halide whereby but two isomers are produced in a controlled fashion in high yields thus yielding an organoleptically acceptable mixture of carboalkoxy norbornane derivatives.

Thus, nothing in the prior art indicates production for organoleptic uses of compounds having the generic structure:

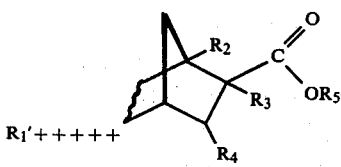

wherein each of the lines + + + + and the wavy line represent single or carbon-carbon double bonds; wherein each of $R_2$, $R_3$ and $R_4$ represents hydrogen or methyl and $R_1'$ represents hydrogen, methyl or methylene; wherein $R_5$ represents $C_1$-$C_4$ alkyl; with the proviso that then $R_2$ is $CH_3$, $R_1'$ is hydrogen and + + + + represents a single bond and the wavy line represents a carbon-carbon single bond or a carbon-carbon double bond; and with the further proviso that when $R_2$ is hydrogen, $R_1'$ is methyl and + + + + represents a carbon-carbon single bond and the wavy line represents a carbon-carbon double bond or a carbon-carbon single bond or $R_1'$ is methylene ($CH_2$) and + + + + is a carbon-carbon double bond and the wavy line is a carbon-carbon single bond.

U.S. Pat. No. 4,143,074 discloses, generically, compounds which are esters and contain the norbornyl moiety having the structures:

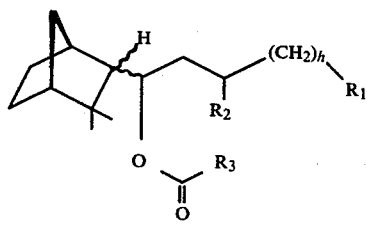

wherein either or both of $R_1$ or $R_2$ is hydrogen or lower alkyl, $R_3$ is hydrogen or lower alkyl and n is zero or 1 and in addition, the compound having the structure:

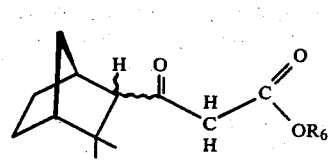

wherein $R_6$ is alkyl having from one up to eight carbon atoms.

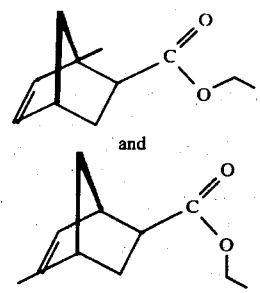

Figure 2:
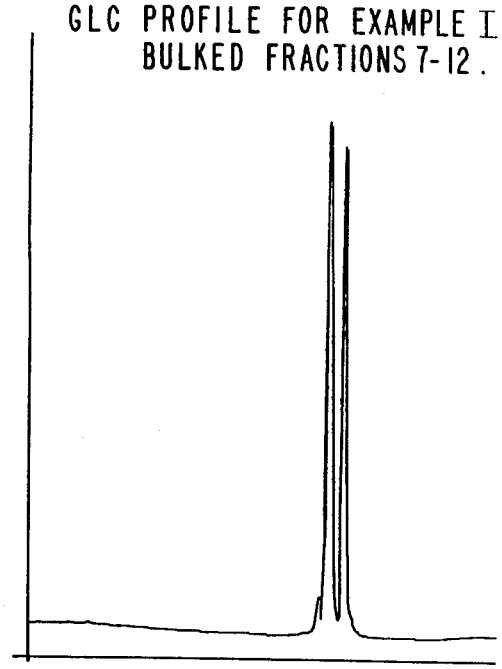

FIG. 2 represents the GLC profile for bulked fractions 7-12 inclusive of the distillation product of the reaction product of Example I (conditions: Carbowax column programmed at 80°-122° C. at 8° C. per minute).

Figure 3A:
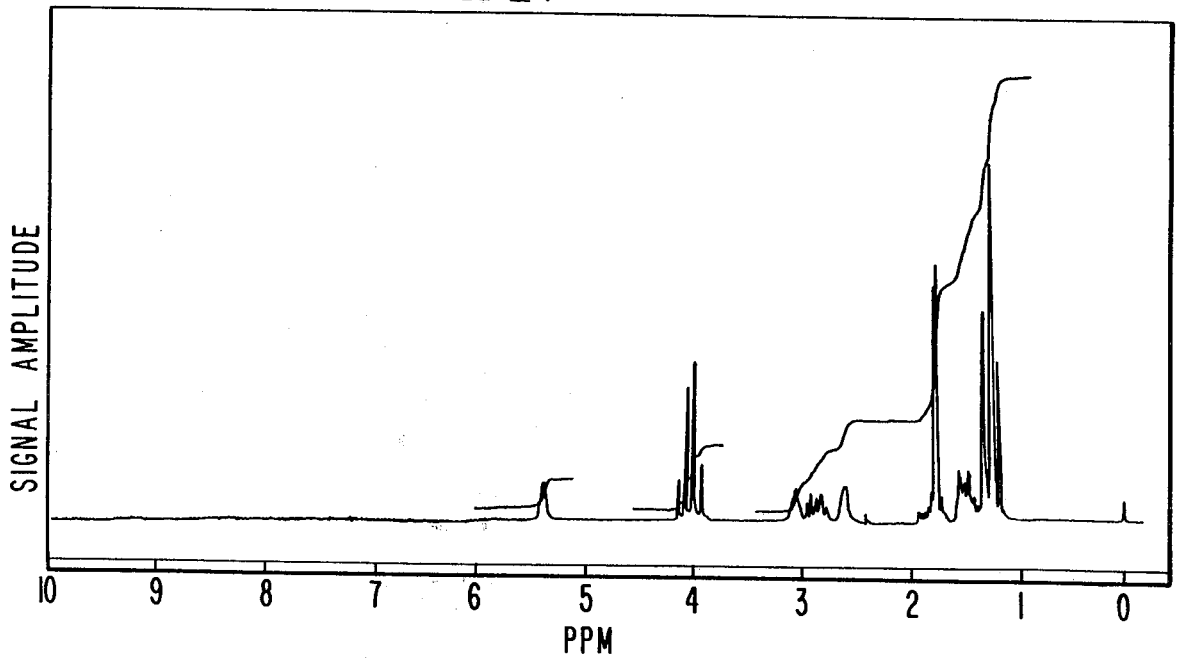

FIG. 3A represents the NMR spectrum for the reaction product of Example I containing the compound having the structure:

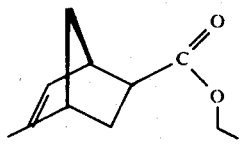

Figure 3B:
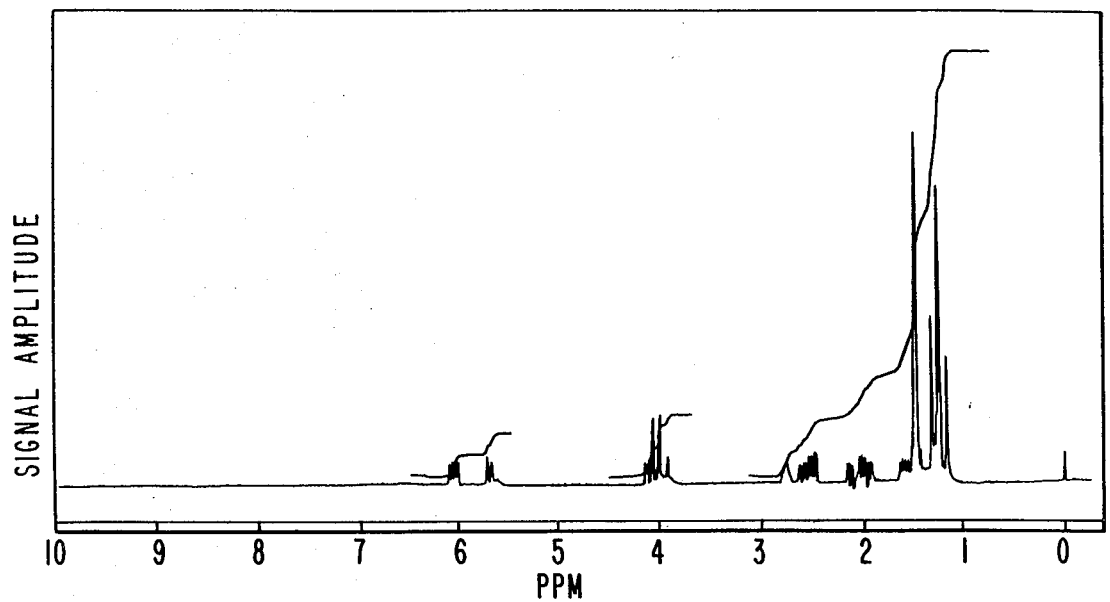

FIG. 3B represents the NMR spectrum for the reaction product of Example I containing the compound having the structure:

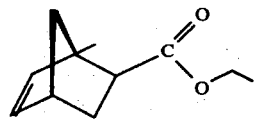

Figure 4A:
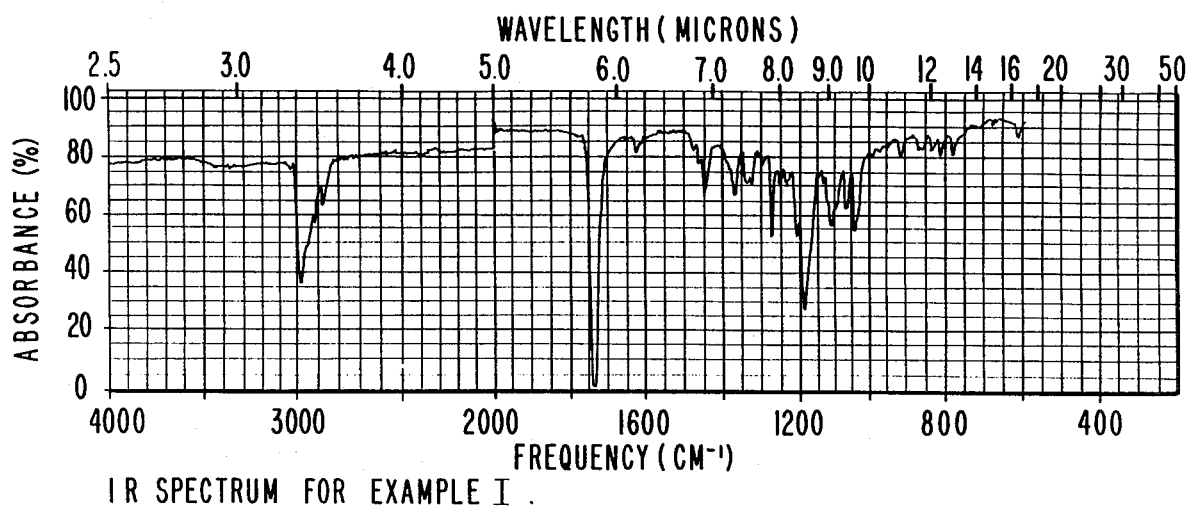

FIG. 4A represents the infrared spectrum for the reaction product of Example I containing the compound having the structure:

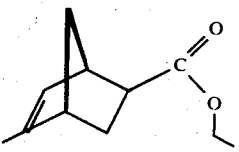

FIG. 4B represents the infrared spectrum for the reaction product of Example I containing the compound having the structure:

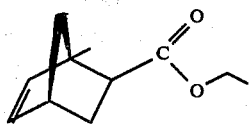

FIG. 5 represents the mass spectrum for the reaction product of Example I containing the compound having the structures:

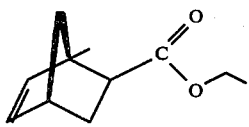

and

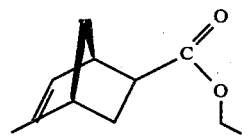

Figure 6:
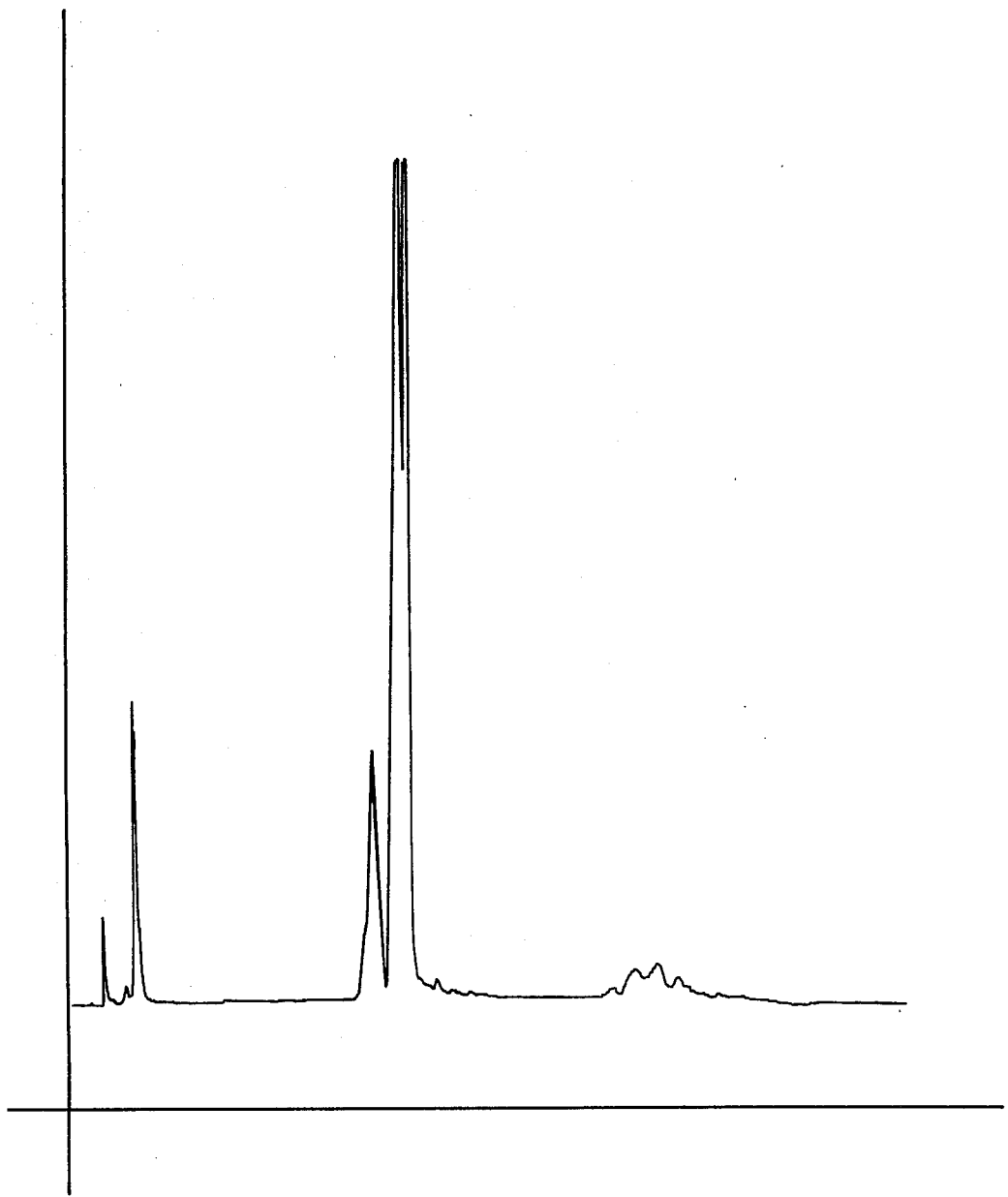

FIG. 6 represents the GLC profile of the crude reaction product (washed before distilling) of Example II containing the compounds having the structures:

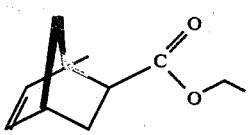

and

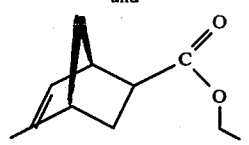

Figure 7:
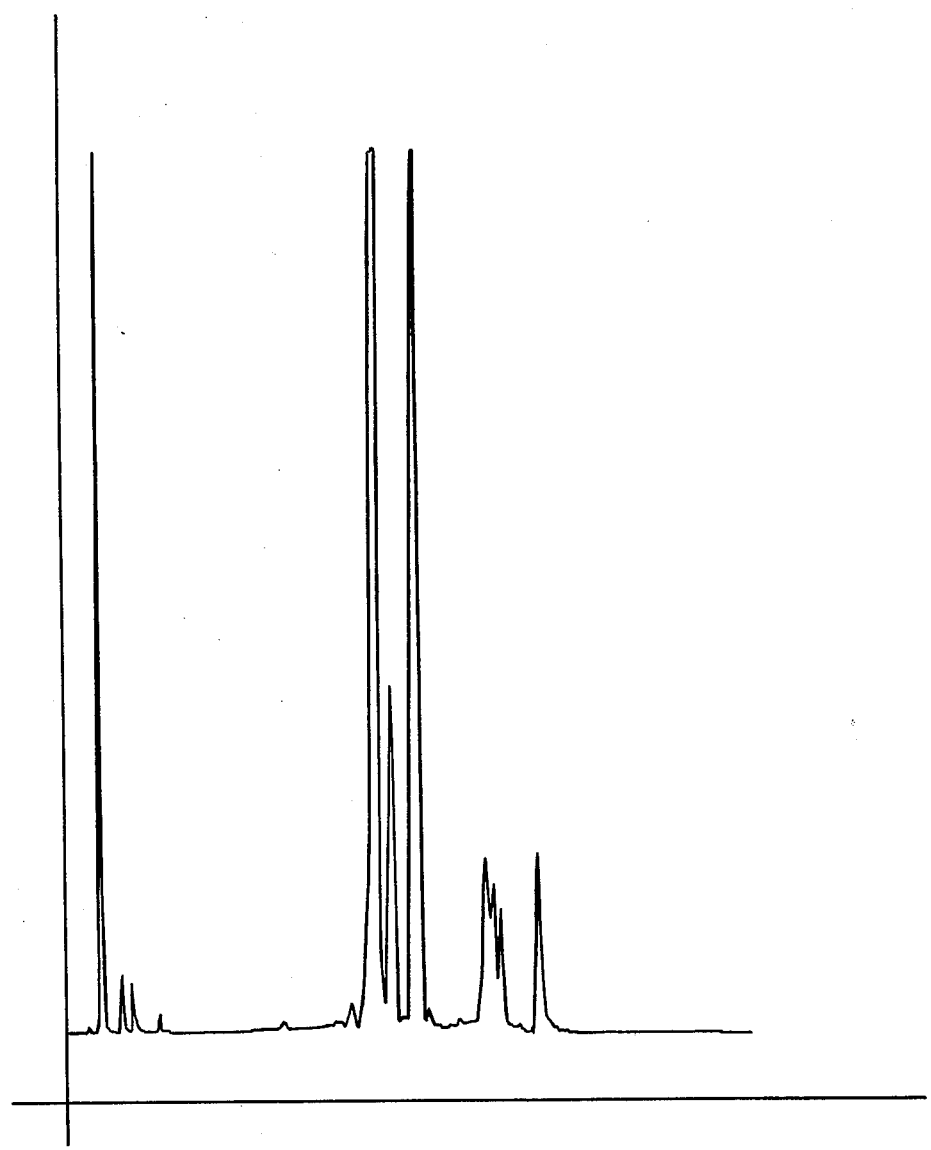

FIG. 7 represents the GLC profile of the reaction product of Example III containing the compounds having the structures:

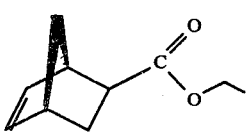

and

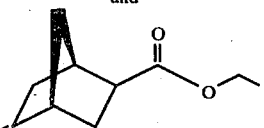

FIG. 8A represents the NMR spectrum for fraction 10 of the distillation product of the reaction product of Example III containing the compound having the structure:

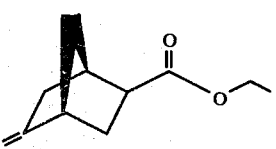

FIG. 8B represents the infrared spectrum for fraction 10 of the distillation product of the reaction product produced according to Example III containing the compound having the structure:

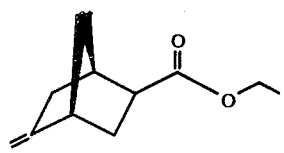

FIG. 9A represents the NMR spectrum for fraction 1 of the distillation product of the reaction product of Example III containing the compound having the structure:

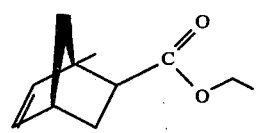

FIG. 9B represents the infrared spectrum for fraction 1 of the distillation product of the reaction product of Example III containing the compound having the structure:

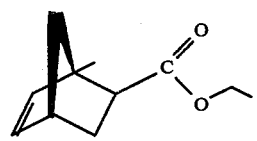

Figure 10:
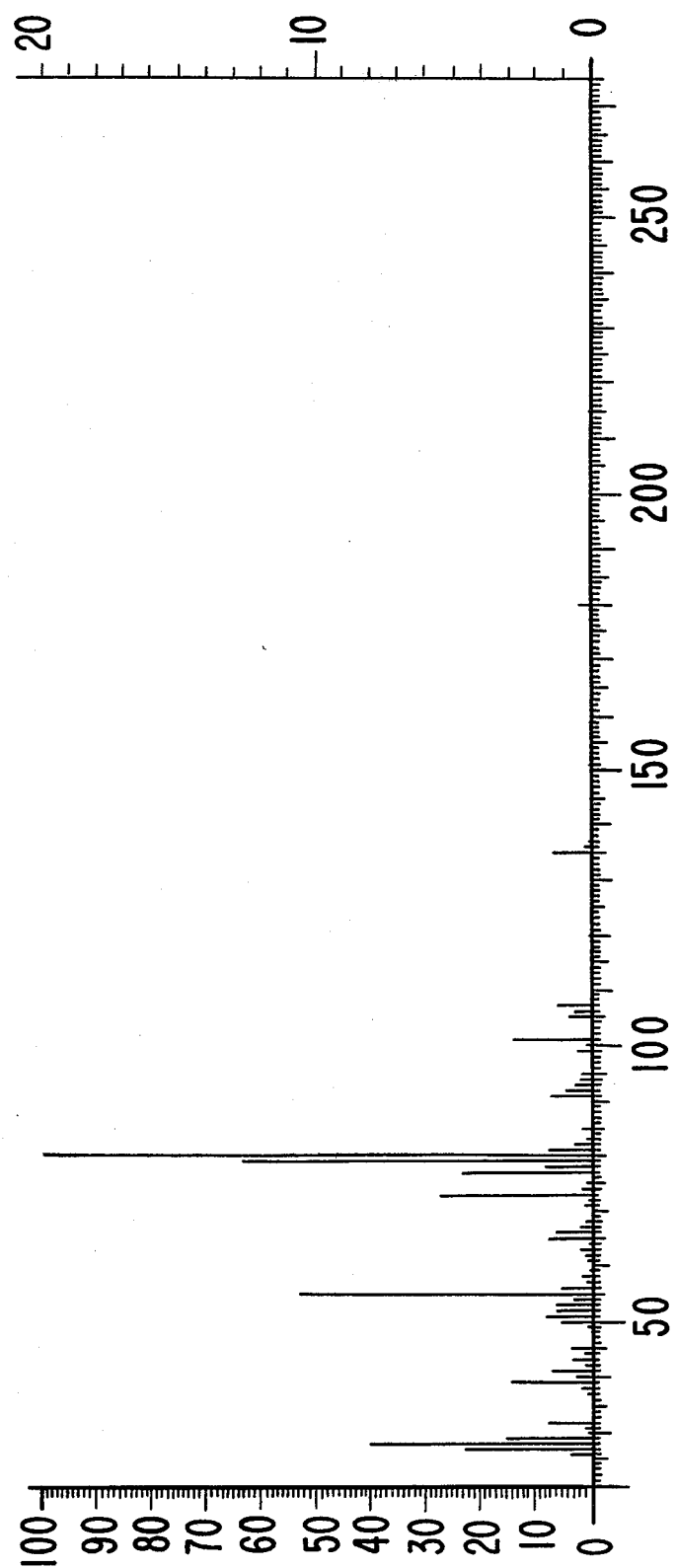

FIG. 10 represents the mass spectrum for the reaction product of Example III containing the compounds having the structures:

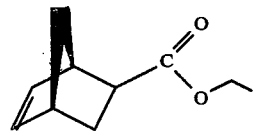

and

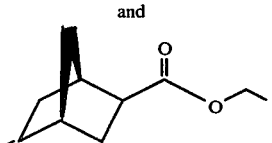

THE INVENTION

It has now been discovered that novel solid and liquid foodstuff, chewing gum, medicinal product and toothpaste compositions and flavoring compositions therefor having the fruity, jasmine-like, burnt fruit, raspberry, green, seedy, sweet, berry-like, red berry-like, blueberry-like, spicy, black pepper-like, herbaceous, clove-like, vermouth-like, strawberry-like and balsamic aroma characteristics and flavor characteristics as well as bitter taste characteristics; as well as novel smoking tobacco and smoking tobacco flavoring compositions having spicy, cooling, clove-like, cinnamon bark-like, sweet, fruity, berry-like, juicyfruit, woody, piney, blueberry, banana, green, herbaceous, strawberry-like and dill aroma and taste prior to and on smoking in both the mainstream and the sidestream; as well as novel perfume compositions, colognes and perfumed articles (e.g. solid or liquid anionic, cationic, nonionic or zwitterionic detergents, fabric softeners and dryer-added fabric softener articles) having intense and long lasting fruity, banana, creamy, camphoraceous, herbaceous, sweet, spicy, woody, eucalyptol-like, rum/butterscotch-like, balsamic, green, minty, borneol-like, and medicinal aromas with strong, chamomile-like, camphor, minty and calamnus-like undertones may be provided by utilization of one or more of the substituted norbornane derivatives having the generic structure:

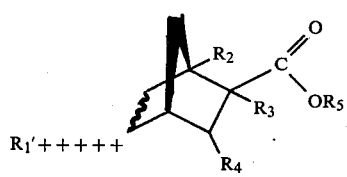

wherein each of the lines + + + + and the wavy line represent single or carbon-carbon double bonds; wherein each of $R_2$, $R_3$ and $R_4$ represents hydrogen or methyl and $R_1'$ represents hydrogen, methyl or methylene; wherein $R_5$ represents $C_1-C_4$ alkyl; with the proviso that when $R_2$ is $CH_3$, $R_1'$ is hydrogen and + + + + represents a single bond and the wavy line represents a carbon-carbon single bond or a carbon-carbon double bond; and with the further proviso that when $R_2$ is hydrogen, $R_1'$ is methyl and + + + + represents a carbon-carbon single bond and the wavy line represents a carbon-carbon double bond or a carbon-carbon single bond or $R_1'$ is methylene ($CH_2$) and + + + + is a carbon-carbon double bond and the wavy line is a carbon-carbon single bond in foodstuffs, chewing gums, toothpastes, medicinal products, perfume compositions, perfumed articles, colognes and smoking tobaccos as well as smoking tobacco substitutes.

Unless otherwise specified, representations herein are intended to indicate "cis" isomers, "trans" isomers, mixtures of "cis" and "trans" isomers and "endo" isomers and "exo" isomers with respect to the norbornane ring moiety and dextro and laevorotatory isomers as well as racemic mixtures of optical isomers of the norbornane derivatives of our invention.

Thus, for example, the generic structure:

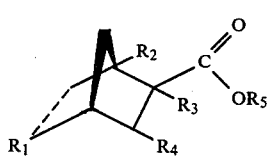

is intended to mean both "endo" and "exo" isomers having the structures:

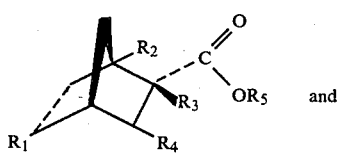

and

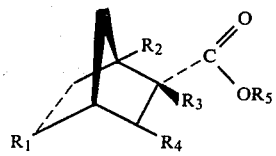

The novel substituted norbornane derivatives of our invention useful as indicated supra may be produced by reacting a 1-methylcyclopentadiene or 2-methylcyclopentadiene having one of the structures:

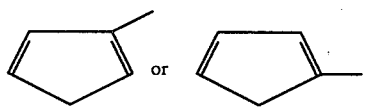

or a mixture of these methylcyclopentadienes defined according to the generic structure:

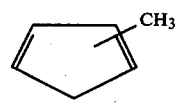

with an alkyl acrylate derivative defined according to the generic structure:

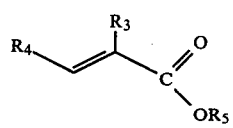

which structure represents a "cis" isomer or a "trans" isomer or a mixture of "cis" and "trans" isomers. Thus, the "trans" isomer may be represented by the structure:

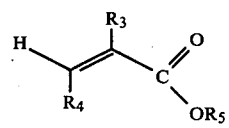

and the "cis" isomer may be represented by the structure:

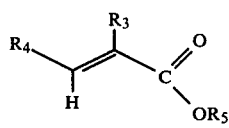

The reaction may be carried out in presence of or in the absence of a catalyst.

When the reaction is carried out in the absence of a catalyst, a mixture is prepared of the compound having the structure:

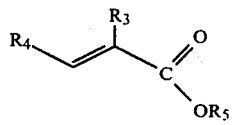

and dimethylbicyclopentadiene which may be represented according to the structure:

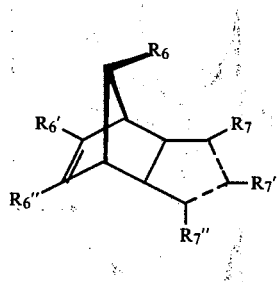

wherein one of $R_6$, $R_6'$ and $R_6''$ represents methyl and the other two of $R_6$, $R_6'$ and $R_6''$ represents hydrogen and wherein one of $R_7$, $R_7'$ and $R_7''$ represents methyl and the other two of $R_7$, $R_7'$ and $R_7''$ represents hydrogen and wherein one of the dashed lines (— — — — —) represents a carbon-carbon double bond and the other of the dashed lines (— — — — —) represents a carbon-carbon single bond, the resulting mixture is heated at a temperature of between about 150° C. and about 250° C., for a period of time of between about 2 hours and about 10 hours whereby, firstly, the dimethylbicyclopentadiene is broken down into a mixture of methylcyclopentadiene isomers and the mixture of methylcyclopentadiene isomers reacts with the ester to form a mixture of compounds having the structures:

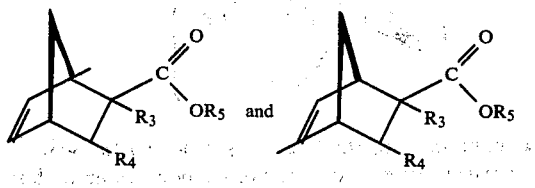

Significantly the yield of these compounds when using the high temperature reaction is greater than when using the catalytic reaction discussed, infra. This higher yield is unexpected, unobvious and advantageous.

However, when a catalyst is used, the catalyst for this reaction may be an alkyl aluminum dihalide or a dialkyl aluminum halide for example $RAlCl_2$ or $R_2AlCl$ wherein R represents methyl, ethyl or n-propyl or i-propyl. The preferred catalyst is ethyl aluminum dichloride. Other Lewis acids such as aluminum trichloride, stannic chloride, zinc chloride, ferric chloride and titanium tetrachloride have been attempted to be used but such attempts have proved to be unsuccessful with minimal or no yields of product being produced. The temperature range of the reaction may vary from about 0° C. up to about 50° C. with ambient temperatures, from 20° up to 30° C. being preferred. The reaction pressure will not affect the yield but conveniently and economically, a reaction pressure of atmospheric is preferred. Thus, the catalyst for the reaction may be defined according to the formula: $R_m' AlCl_n$ wherein R' is $C_1$-$C_3$ alkyl and the sum, m+n, equals 3; with m being one or two and n being one to two. The resulting reaction mass is a mixture of compounds containing unsaturation in the norbornane moiety, defined according to the generic structure:

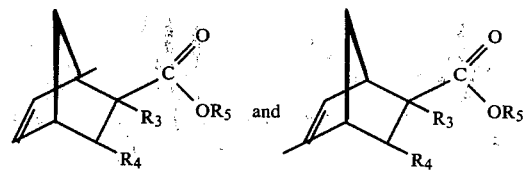

These compounds may be used "as is" for their organoleptic properties, or the mixture of compounds may be further reacted by means of rearrangement reaction or by means of hydrogenation reaction.

When the compounds are reacted by means of rearrangement reaction, the rearrangement reaction causes compounds having the structure:

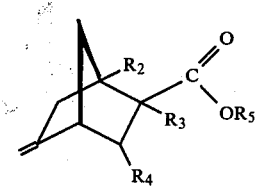

(wherein $R_2$ is hydrogen and $R_3$, $R_4$ and $R_5$ are as defined above) to be formed. The individual rearrangement reaction taking place is illustrated as follows:

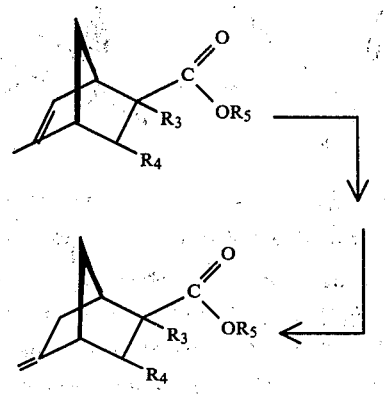

This rearrangement is carried out by reacting the compounds defined according to the structure:

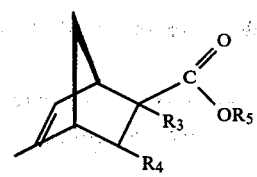

with rearrangement agents such as boron trifluoride-diethyl-ether complex at a temperature in the range of from about 0° C. up to about 15° C., with a preferred temperature in the range of from 5° up to 10° C. The reaction is to take place in the presence of an inert solvent such as toluene or xylene, which solvent is mixable with the reactants having the structures:

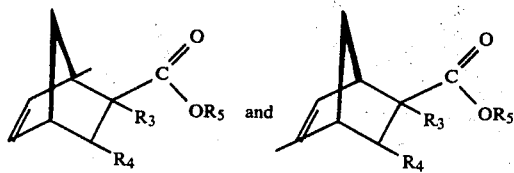

and is also mixable with the boron trifluoride etherate or other rearrangement reagent. The resulting compounds have unexpected, unobvious and advantageous organoleptic properties.

The compounds having the structures:

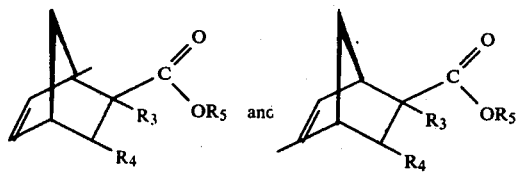

also may be further hydrogenated using hydrogen gas at super atmospheric pressure. The hydrogenation is carried out to yield compounds having the structures:

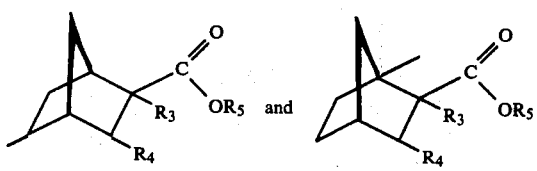

It is preferable to carry out the hydrogenation at pressures of from about 20 psig up to about 2,000 psig with a pressure range of from about 40 to about 80 psig being preferred. It is also preferable for the reaction to be carried out in the presence of a catalyst such as Raney Nickel, palladium on carbon, palladium on calcium carbonate, palladium on barium sulfate and platinum. When using the palladium-salt catalyst it is preferred to use from about 3% up to about 12% palladium on salt, for example 5% palladium on calcium carbonate.

Thus, the reaction sequence which is embodied within our invention may be illustrated as follows:

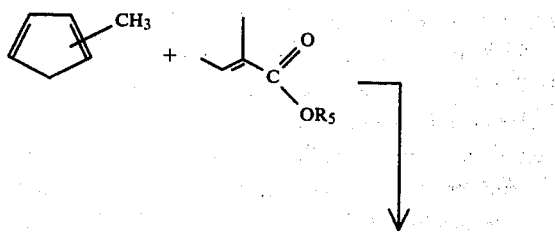

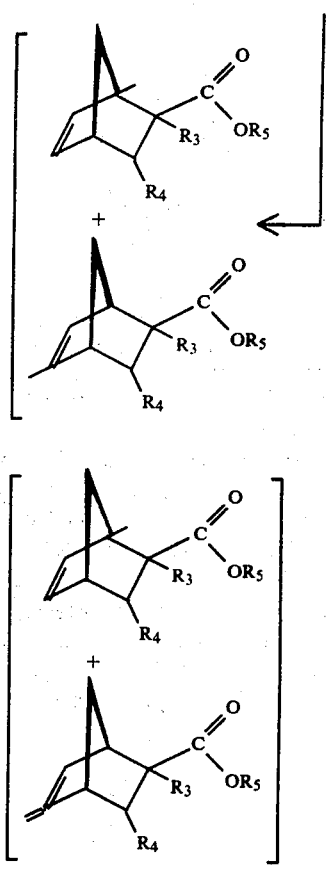

wherein each of the lines $++++$ and the wavy line represent single or carbon-carbon double bonds; wherein each of $R_2$, $R_3$ and $R_4$ represents hydrogen or methyl and $R_1'$ represents hydrogen, methyl or methylene; wherein $R_5$ represents $C_1$-$C_4$ alkyl; with the proviso that when $R_2$ is $CH_3$, $R_1'$ is hydrogen and $++++$ represents a single bond and the wavy line represents a carbon-carbon single bond or a carbon-carbon double bond; and with the further proviso that when $R_2$ is hydrogen, $R_1'$ is methyl and $++++$ represents a carbon-carbon single bond and the wavy line represents a carbon-carbon double bond or a carbon-carbon single bond or $R_1'$ is methylene ($CH_2$) and $++++$ is a carbon-carbon double bond and the wavy line is a carbon-carbon single bond.

The following tables set forth the product produced by the processes covered by our invention and the alkyl acrylate precursor reactant starting material to be reacted with the methylcyclopentadienes to produced such products and in addition, sets forth the organoleptic properties of the products produced by the process of our invention:

TABLE I

| Alkylacrylate Reactant | Reaction Product Names | Reaction Product Structures |
|---|---|---|
| Methyl- crotonate | Methyl ester of 1,3- and 3,5-dimethyl norbornene-2- carboxylic acid | (structure) and |

TABLE I-continued

| Alkylacrylate Reactant | Reaction Product Names | Reaction Product Structures |
|---|---|---|
| | | 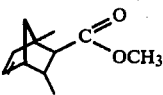 |
| Methyl-crotonate | Methyl ester of 1,3- and 3,5-dimethyl norbornene-2-carboxylic acid | 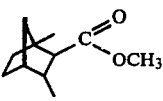 and 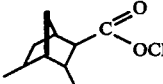 |
| Ethyl-crotonate | Ethyl ester of 1,3- and 3,5-dimethyl norbornene-2-carboxylic acid | 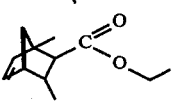 and 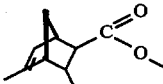 |
| Ethyl-acrylate | Ethyl ester of 1- and 5-methyl-5-norbornene-2-carboxylic acid | 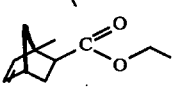 and 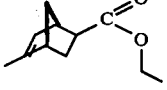 |
| Ethyl-acrylate | Ethyl ester of 1- and 5-methyl-norbornane-2-carboxylic acid | 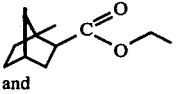 and 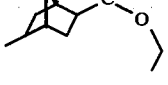 |

TABLE I-continued

| Alkylacrylate Reactant | Reaction Product Names | Reaction Product Structures |
|---|---|---|
| n-Butylacrylate | n-Butyl ester of 1- and 5-methyl-5-norbornene-2-carboxylic acid | 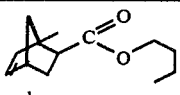 and 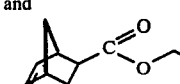 |
| Ethyl-methacrylate | Ethyl esters of 1,2- and 2,5-dimethyl-5-norbornene-2-carboxylic acid | 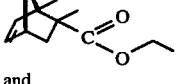 and 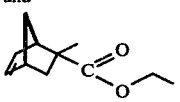 |
| Ethyl-crotonate | Ethyl ester of 1,3- and 3,5-dimethyl norbornane-2-carboxylic acid | 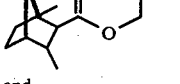 and 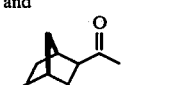 |
| Ethyl-acrylate | Ethyl ester of 1-methyl-5-norbornene-2-carboxylic acid and ethyl ester of 5-methylene-norbornane-2-carboxylic acid | 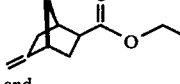 and 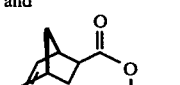 |

TABLE II

| Reaction Product Name | Fragrance Properties | Food Flavor Properties | Smoking Tobacco Flavor Properties |
|---|---|---|---|
| Methyl ester of 1,3- and 3,5-dimethyl norbornene-2-carboxylic acid | A fruity, banana, creamy aroma with camphoraceous and minty undertones | A burnt fruit aroma and taste at 0.1 ppm | Sweet, fruity, berry-like, woody aroma prior to smoking and a sweet, fruity aroma on smoking both in the main- and sidestreams |
| Methyl ester of 1,3- and 3,5-dimethyl norbornane-2-carboxylic acid | A fruity, camphoraceous and herbaceous aroma | A fruity and blackberry-like aroma and taste at 0.1 ppm | Prior to smoking a sweet, woody, spicy, cooling and clove-like aroma profile; and on smoking a sweet, spicy, cooling and woody aroma and taste in both the main stream and the side stream |
| Ethyl ester of 1,3- and 3,5-dimethyl norbornene-2-carboxylic acid | A sweet, spicy herbal, woody, eucalyptol-like aroma profile with a distinct calamnus undertone | A sweet, fruit, berry-like, spicy, black pepper-like, herbaceous, clove-like aroma and taste profile at 10 ppm | A sweet, fruity, berry, spicy, cinnamon bark-like and clove-like aroma and taste profile prior to and on smoking in the main stream and |

TABLE II-continued

| Reaction Product Name | Fragrance Properties | Food Flavor Properties | Smoking Tobacco Flavor Properties |
|---|---|---|---|
| | | causing it to be useful in blueberry, tobacco, clove and raspberry flavor foodstuffs | the side stream |
| Ethyl ester of 1- and 5-methyl-5-norbornene-2-carboxylic acid | A sweet, fruity (banana-like) creamy and minty aroma profile with the minty notes outstanding on dryout | A sweet, fruity red berry-like, raspberry and seedy aroma and taste profile with an additional strawberry taste nuance at 0.02 ppm causing it to be useful in red berry, cherry, raspberry and strawberry flavors | A fruity, banana like, green and strawberry-like aroma and taste both prior to and on smoking in the main stream and in the side stream |
| Ethyl ester of 1- and 5-methyl-5-norbornene-2-carboxylic acid | A, fruity, banan like, and creamy aroma profile | A sweet, fruity, raspberry, vermouth-like and blueberry aroma with fruit, raspberry and blueberry taste characteristics at 0.01 ppm and at 1 ppm causing it to be useful for vermouth, blueberry and raspberry flavors and mouthwash and toothpaste flavors | A sweet, fruity, "juicyfruit", woody, piney, and blueberry aroma and taste profile prior to and on smoking in the mainstream and in the side stream |
| n-Butyl ester of 1- and 5-methyl-5-norbornene-2-carboxylic acid | A balsamic and rum/butterscotch aroma profile | A fruity, strawberry, blueberry and balsamic aroma profile with blueberry, balsamic and bitter taste characteristics at 2 ppm | An earthy, mushroom aroma prior to and on smoking |
| Ethyl esters of 1,2- and 2,5-dimethyl-5-norbornene-2-carboxylic acid | A green, minty, borneol-like, spicy, somewhat medicinal aroma profile reminiscent of pepacuana boric extract | A fruit, raspberry and seedy aroma and taste profile with additional bitter taste nuances at 0.2 ppm | A sweet, green, herbaceous, dill and fruity aroma and taste profile both prior to and on smoking in mainstream and in the side stream |
| Ethyl esters of 1,3- and 3,5-dimethyl-5-norbornane-2-carboxylic acid | A fruity, piney, herbaceous and cassis aroma profile with calamnus undertones | A fruity, blueberry and herbaceous aroma character with a sweet, fruity and blueberry flavor characteristic at 0.02 parts per million | |
| Ethyl ester of 1-methyl-5-norbornene-2-carboxylic acid and the ethyl ester of 5-methylene-norbornane-2-carboxylic acid | A sweet, fruity green, somewhat herbaceous aroma with chamomile-calamnus notes; a long lasting strong intensity after 7 hours | A seedy, strawberry, green, fresh, jasmine-like aroma and flavor characteristic at 0.02 ppm causing it to be useful in strawberry, berry, mango and tropical | |

TABLE II-continued

| Reaction Product Name | Fragrance Properties | Food Flavor Properties | Smoking Tobacco Flavor Properties |
| --- | --- | --- | --- |
| | | fruit flavors | |

When the norbornane derivatives of our invention are used as food flavor adjuvants, the nature of the co-ingredients included with each of the said norbornane derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually to, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers of softening agents, e.g., glycerine; and a flavor compostion which incorporates one or more of the norbornane derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2-and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents includes emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar the the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include aldehydes, esters, natural oils, alcohols, sulfides, ketones, lactones, carboxylic acids and hydrocarbons such as heliotropin, terpinenol-4, benzaldehyde, anisaldehyde, phenyl acetaldenyde, benzyl formate, benzyl acetate, cis-3-hexenyl benzoate, methyl hexanoate, hexanal, eucalyptol, eugenol, acetaldehyde, ethyl acetate, ethyl butyrate, turpentine gum oil, limonene, gum camphor, isobornyl acetate, borneol, cinnamic aldehyde, cuminic aldehyde, furfural, methyl cinnamate, cassia oil, vanillin, maltol, parahydroxybenzyl acetate, dimethyl sulfide, alphaionone, acetic acid, isobutyl acetate, acetone, butyric acid, formic acid, valeric acid, amyl acetate, amyl butyrate, anethol, benzyl salicylate, diacetyl, dimethyl anthranilate, ethyl methylphenylglycidate, ethyl succinate, ethyl valerate, geraniol, cis-3-hexen-1-ol, 2-hexenyl acetate, 2-hexenyl butyrate, hexyl butyrate, 4-(p-hydroxyphenyl)-2-butanone, betaionone, isobutyl cinnamate, jasmine, lemon essential oil, methyl butyrate, methyl caproate, methyl disulfide, methyl p-napthyl ketone, orris butter, rose absolute, terpenyl acetate, gamma-undecalactone, vanilla and alcohol.

The specific flavoring adjuvant selected for use may be either solid or liquid depending upon the desired physical form of the ultimate product, i.e., foodstuff, whether simulated or natural, and should, in any event, (i) be organoleptically compatible with the norbornane derivatives of our invention by not covering or spoiling the organoleptic properties (aroms and/or taste) thereof; (ii) be non-reactive with the norbornane derivatives of our invention and (ii) be capable of providing an environment in which the norbornane derivatives can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of norbornane derivatives employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify, or enhance the organoleptic characteristics of the parent composition, whether foodstuff per se, chewing gum, per se, medicinal product per se, toothpaste per se, or flavoring composition.

The use of insufficient quantities of norbornane derivatives will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of norbornane derivatives ranging from a small but effective amount, e.g., 0.005 parts per million up to about 100 parts per million based on total composition are suitable. Concentrations in excess of the maximum quantity stated are not normally recommended, since they fail to prove commensurate enhancement of organoleptic properties. In those instances, wherein the norbornane derivatives are added to the foodstuff as an integral component of a flavoring composition, it is, of course, essential that the total quantity of flavoring composition employed be sufficient to yield an effective norbornane derivative concentration in the foodstuff product.

Food flavoring compositions prepared in accordance with the present invention preferably contain the norbornane derivatives in concentrations ranging from about 0.01% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the norbornane derivatives with, for example, gum arabic, gum tragacanth, carrageenan and the like, and thereafter spray-drying the resultant mixture whereby to obtain the particular solid product. Preprepared flavor mixes in powder form e.g., a fruit-flavored powder mix are obtained by mixing the dried solid components, e.g., starch, sugar and the like and norbornane derivatives in a dry blender until the requisite degree of uniformity is achieved.

It is presently preferred to combine with the norbornane derivatives of our invention, the following adjuvants:
Heliotropin;
Terpinenol-4;
Benzaldehyde;
Anisaldehyde;
Phenylacetaldehyde;
Benzyl formate;
Benzyl acetate;
Cis-3-hexenyl benzoate;
Methyl hexanoate;
Hexanal;
Eucalyptol;
Eugenol;
Acetaldehyde;
Ethyl acetate;
Ethyl butyrate;
Turpentine gum oil;
Limonene;
Gum camphor;
Isobornyl acetate;
Borneol;
Cinnamic aldehyde;
Cuminic aldehyde;
Furfural;
Methyl cinnamate;
Cassia oil;
Vanillin;
Malto;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;

2-Hexenyl butyrate;
Hexyl butyrate;
4-(p-Hydroxyphenyl)-2-butanone;
Beta-ionone;
Isobutyl cinnamate;
Jasmine;
Lemon essential oil;
Methyl butyrate;
Methyl capronate;
Methyl disulfide;
Methyl p-naphthyl ketone;
Orris butter;
Rose Absolute;
Terpenyl acetate;
Gamma-undecalactone;
Vanilla; and
Alcohol.

An additional aspect of our invention provides an organoleptically improved smoking tobacco product and additives therefor, as well as methods of making the same which overcome problems heretofore encountered in which desired spicy, cooling, clove-like, cinnamon bark-like, sweet, fruity, berry-like, juicyfruit, woody, piney, blueberry, banana, green, herbaceous, strawberry-like, and dill flavor characteristics of natural tobacco (prior to smoking and, on smoking, in the mainstream and in the sidestream) as well as cooling effects, are created or enhanced or modified or augmented and may be readily controlled and maintained at the desired uniform level regardless of variations in the tobacco components of the blend.

This invention further provides improved tobacco additives and methods whereby various desirable natural aromatic tobacco flavoring characteristics with spicy, cooling, clove-like, cinnamon bark-like, sweet, fruity, berry-like, juicyfruit, woody, piney, blueberry, banana, green, herbaceous, strawberry-like and dill notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more norbornane derivatives of our invention.

In addition to the norbornane derivatives of our invention other flavoring and aroma additives may be added to the smoking tobacco material or substitute therefor either separately or in mixture with the norbornane derivatives as follows:

I. Synthetic Materials

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b)furan
4-Hydroxyhexanoic acid, gamma lactone; and
Polyisoprenoid hydrocarbons defined in Example V of U.S. Pat. No. 3,589,372, issued on June 29, 1971.

II. Natural Oils

Celery seed oil;
Coffee extract;
Bergamot oil;
Cocoa extract;
Nutmeg oil; and
Origanum oil;

An aroma and flavoring concentrate containing one or more norbornane derivatives of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of spicy and/or cooling and/or clove-like and/or cinnamon bark-like and/or sweet and/or fruity and/or berry-like and/or juicyfruit and/or woody and/or piney and/or blueberry and/or banana and/or green and/or herbaceous and/or strawberry-like and/or dill notes, we have found that satisfactory results are obtained if the proportion by weight of the sum total of norbornane derivative(s) to smoking tobacco material is between 50 ppm and 1,500 ppm (0.015%–0.15%). We have further found that satisfactory results are obtained if the proportions by weight of the sum total of norbornane derivative used to flavoring material is between 1,500 and 15,000 ppm (0.15%–1.5%).

Any convenient method for incorporating the norbornane derivative(s) into the tobacco product may be employed. Thus, the norbornane derivative(s) taken alone or along with other flavoring additives may be dissolved in a suitable solvent such as ethanol, diethyl ether and/or volative organic solvents and the resulting solution may either be spread on the cured, cased and blended tobacco material or the tobacco material may be dipped into such solution. Under certain circumstances, a solution of the norbornane derivative(s) taken alone or taken further together with other flavoring additives as set forth above, may be applied by means of a suitable applicator such as a brush or roller on the paper or leaf wrapper for the smoking product, or it may be applied to the filter by either spraying; or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated by have the norbornane derivative(s) in excess of the amounts or concentrations above indicated so that when blended with other tobaccos, the final product will have the precentage within the indicated range.

In accordance with one specific example of our invention an aged, cured and shredded domestic burley tobacco is sprayed with a 20% ethanol solution of the mixture of 1,3- and 3,5-dimethyl-2-norbornane carboxylic acid methyl esters having the structures:

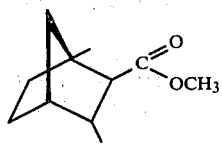

and

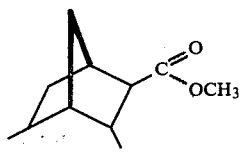

in an amount of mixture to provide tobacco composition containing 800 ppm by weight of the mixture of the two esters on a dry basis. Thereafter the alcohol is removed by evaporation and the tobacco is manufactured into cigarettes by the usual techniques. The cigarette when treated as indicated has a desired and pleasing aroma which is detectable in the mainstream and the sidestream when the cigarette is smoked. This aroma is described as being sweeter, more aromatic, more tobacco-like having sweet, spicy, cooling, woody and clove-like notes.

While our invention is particularly useful in the manufacture of smoking tobacco, such as cigarette tobacco, cigar tobacco and pipe tobacco, other tobacco products, formed from sheeted tobacco dust or fines may also be used. Likewise, the norbornane derivative(s) of our invention can be incorporated with materials such as filter tip materials (e.g. cellulose acetate filters wherein spicy, cooling, clove-like, cinnamon bark-like, sweet, fruity, berry-like, juicyfruit, woody, piney, blueberry, banana, green herbaceous, stawberry-like and/or dill effects are desired), seam paste, packaging materials and the like which are used along with tobacco to form a product adapted for smoking. Furthermore, the norbornane derivative(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The norbornane derivative(s) and one or more auxiliary perfume ingredients, including, for example, hydrocarbons, alcohols, ketones, aldehydes, nitriles, esters, lactones or cyclic esters, synthetic essential oils and natural essential oils, may be admixed so that the combined odors of the individual components produce a pleasant and desired fragrance, particularly and preferably in fruity, banana, creamy, camomile-like, camphoraceous, herbaceous, sweet, spicy, woody, eucalyptol-like, rum/buttersotch, balsamic, green, and/or minty fragrances. Such perfume compositions usually contain (a) the main note or the "bouque" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more of the norbornane derivative(s) of our invention can be used to alter, modify or enhance the aroma characteristics of a perfume composition, for example, by utilizing or moderating the olfactory reaction contributed by another ingredient in the composition.

The amount of norbornane derivative(s) of our invention which will be effective in perfume compositions as well as perfumed articles and colognes depends on many factors, including the other ingredients, their amounts and the effects which are desired. It has been found that perfume compositions containing as little as 0.01% of norbornane derivative(s) or even less (e.g., 0.005%) can be used to impart a fruity, banana, creamy, camphoraceous, herbaceous, sweet, spicy, woody, eucalyptol-like, rum/butterscotch, balsamic, green, minty, borneol-like and/or medicinal odor with camphor, minty and calamnus-like nuances to soaps, detergents (including anionic, nonionic, cationic and zwitterionic solid or liquid detergents), cosmetics, fabric softeners, dryer-added fabric softener articles, fabric whiteners and optical brighteners or other products. The amount employed can range up to 70% of the fragrance components and will depend on considerations of cost, nature of the end product, the effect desired on the finished product and the particular fragrance sought.

The norbornane derivative(s) of our invention are useful (taken alone or together with other ingredients in perfume compositions) in detergents and soaps, space odorants and deodorants, perfumes, colognes, toilet water, hair preparations, such as lacquers, brilliantines, pomades and shampoos; cosmetic preparations, such as creams, deodorants, hand lotions and sun screens; powders such as talcs, dusting powders, face powders and the like. As little as 0.01% of the norbornane derivative(s) will be suffice to impart an intense fruity, banana, creamy, chamomile-like, camphoraceous, herbaceous, sweet, spicy, woody, eucalyptol-like, rum/butterscotch, balsamic, green, minty, borneol-like and/or medicinal note to various types of perfume formulations including the woody perfume formulations. Generally no more than 3% of the norbornane derivative(s) based on the ultimate end product (perfumed article) is required.

In addition, the perfume composition or fragrance composition of our invention can contain a vehicle, or carrier for the norbornane derivative(s). The vehicle can be a liquid such as a non-toxic alcohol, a non-toxic glycol, or the like. The carrier can also be an absorbent solid, such as a gum (e.g., gum arabic), or components for encapsulating the composition (such as gelatin).

It will thus be apparent that the norbornane derivative(s) of our invention can be utilized to alter, modify or enhance sensory properties, particularly organoleptic properties such as flavor(s) and/or fragrance(s) of a wide variety of consumable materials.

The following examples serve to illustrate processes for specifically producing the norbornane derivative(s) useful in our invention.

The following examples also serve to illustrate specific embodiments of our invention.

It will be understood that these examples are illustrative and the invention is to be considered to be restricted thereto only as indicated in the appended claims.

All parts and percentages given herein are by weight unless otherwise specified.

EXAMPLE I

Preparation of ethyl esters of 1- and 5-methyl-5-norbornene-2-carboxylic acids

Reaction:

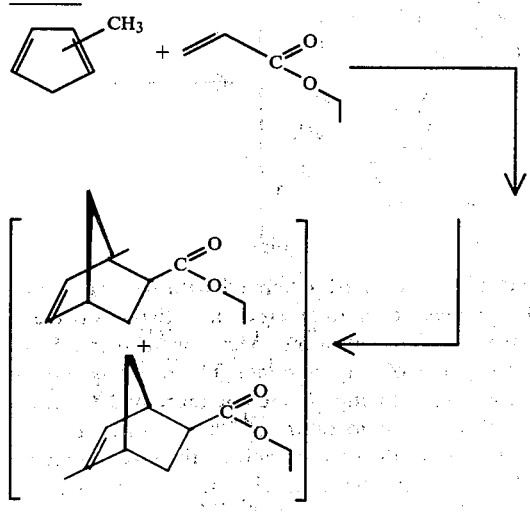

Into a three liter flask equipped with thermometer, stirrer, condenser, addition funnel, cooling bath and nitrogen purge are placed one gram of hydroquinone, 1000 ml toluene and 50 grams of 25% ethyl aluminum dichloride dissolved in anhydrous toluene. The reaction mass is cooled to about 10° C. and, over a period of 30 minutes, 600 grams of ethyl acrylate is added to the resulting mixture. During the addition the temperature of the mixture is maintained at between 10° C. and 14° C.

Over a period of three hours while maintaining the reaction temperature at 20°-23° C., 389 grams of a mixture of 1-methyl-1,3-cyclopentadiene and 2-methyl-1,3-cyclopentadiene is added to the reaction mixture. At the end of the three hour period GLC analysis indicates the reaction to be complete.

The resulting reaction mass is poured into one liter of 10% aqueous hydrochloric acid. The reaction mass now exists in two phases; an organic phase and an aqueous phase. The aqueous phase is separated from the organic phase and the organic phase is washed as follows:

A. One 1 liter portion of water;
B. One 1 liter portion of saturated sodium bicarbonate solution;
C. One 1 liter portion of water;
D. One 1 liter portion of water.

The pH of the resulting washing is about six.

The resulting organic layers are combined and the toluene is stripped off under vacuum. Calcium carbonate and Primol ® is added to the reaction mass and the reaction mass is distilled yielding the following fractions on a 12 inch Goodloe column:

| Fraction No. | Vapor Temp. (°C.) | Liquid Temp. (°C.) | mm/Hg. Pressure | Reflux Ratio | Weight of Fraction (g.) |
|---|---|---|---|---|---|
| 1 | 48/48 | 63/65 | 3.0/3.0 | 9:1 | 23.8 |
| 2 | 50 | 64 | 3.0 | 9:1 | 19.3 |
| 3 | 50 | 64 | 2.8 | 9:1 | 20.5 |
| 4 | 53 | 64 | 2.6 | 9:1 | 19.1 |
| 5 | 54 | 64 | 2.6 | 9:1 | 20.2 |
| 6 | 55 | 65 | 2.8 | 9:1 | 19.9 |
| 7 | 56 | 66 | 2.7 | 9:1 | 25.2 |
| 8 | 54 | 66 | 2.5 | 9:1 | 21.7 |
| 9 | 54 | 66 | 2.5 | 9:1 | 48.6 |
| 10 | 54 | 66 | 2.5 | 9:1 | 55.8 |
| 11 | 54 | 67 | 2.5 | 9:1 | 48.7 |
| 12 | 57 | 77 | 2.5 | 9:1 | 59.7 |
| 13 | 57 | 77 | 2.5 | 9:1 | 47.2 |
| 14 | 57 | 87 | 2.5 | 9:1 | 58.0 |
| 15 | 55/58 | 87/108 | 2.5/2.5 | 4:1 | 33.0 |
| 16 | 45 | 110 | 3.0 | 4:1 | 6.6 |

Fractions 7-12 are bulked and NMR, IR and mass spectral analysis yield the information that these fractions consist essentially of a mixture of compounds having the structures:

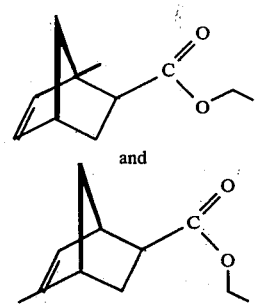

Figure 1:
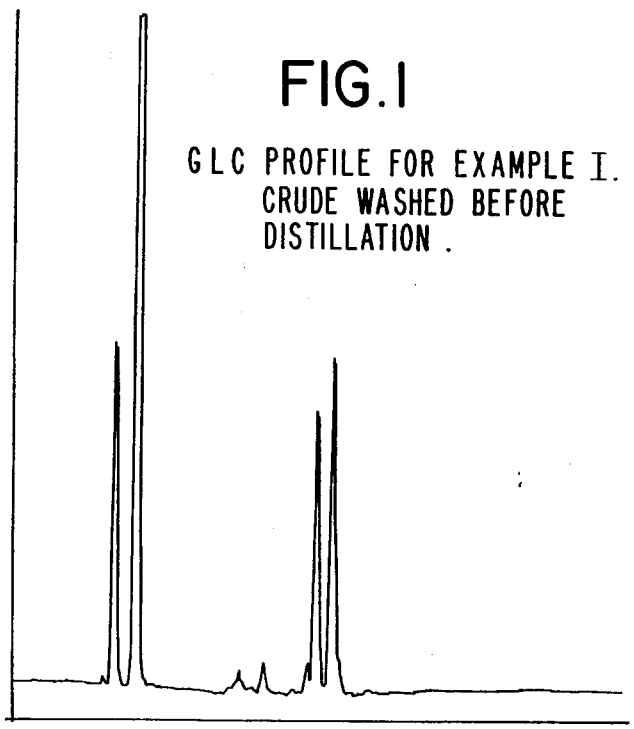
FIG. 1 represents the GLC profile of the crude reaction product (washed before distilling) of Example I containing the compounds having the structures.

FIG. 1 is the GLC profile of the crude reaction product washed, but before distilling. (Conditions: Carbowax column programmed at 80°-122° C. at 8° C. per minute).

FIG. 2 is the GLC profile of fractions 7-12 from the foregoing distillation, bulked.

FIG. 3A is the NMR spectrum for the compound having the structure:

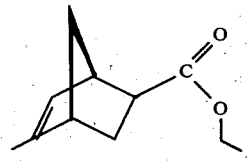

FIG. 3B is the NMR spectrum for the compound having the structure:

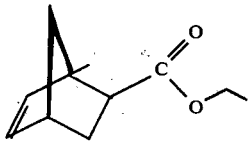

FIG. 4A is the infrared spectrum for the compound having the structure:

FIG. 4B is the infrared spectrum for the compound having the structure:

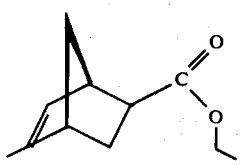

FIG. 5 is the mass spectrum for the mixture of compounds having the structures:

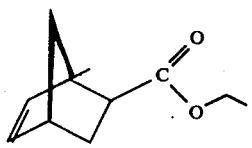

and

The mixture of compounds having the structures:

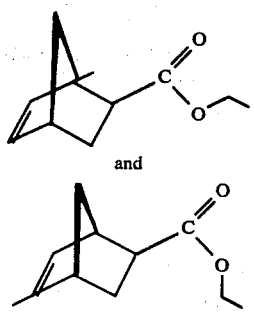

and from a fragrance standpoint has a sweet, fruity (banana-like) and creamy aroma profile with minty nuances intense on dryout.

From a food flavor standpoint, the resulting mixture has a sweet, fruity, red berry, raspberry and seedy aroma and taste and in addition a strawberry taste at 0.02 ppm. Thus, this material is useful in red berry, cherry, raspberry and strawberry flavored foodstuffs.

The resulting mixture has a fruity, banana, green and strawberry-like aroma and taste both prior to and on smoking smoking tobacco articles in both the mainstream and the sidestream.

EXAMPLE II

Preparation of ethyl ester of 1- and 5-methyl-5-norbonene-2-carbonylic acids without the use of catalysts Reaction:

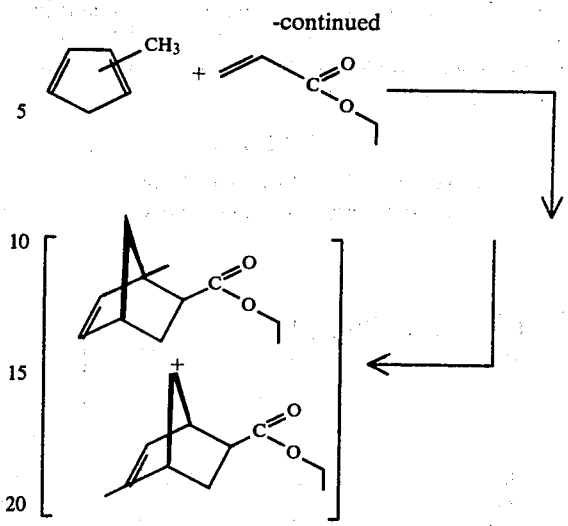

Into a two liter flask equipped with heating mantel, reflex condenser, thermomether and stirrer is placed a mixture of 400 grams of methylcyclopentadiene dimer, and 500 grams of ethyl acrylate. The resulting mixture is heated, with stirring, to a temperature of 200° C. and maintained at a temperature of 200° C. for a period of six hours. After the six hour period, the reaction mass is cooled and work up according to the procedure of Example I.

The resulting worked up product is then admixed with 10 grams of Primol ® and distilled yielding the following fractions:

| Fraction No. | Vapor Temp. (°C.) | Liquid Temp. (°C.) | mm/Hg Pressure | Reflux Ratio | Weight of Fraction (g.) |
| --- | --- | --- | --- | --- | --- |
| 1 | 53/60 | 84/80 | 1.8/3.0 | 4:1 | 51 |
| 2 | 60 | 82 | 3.0 | 4:1 | 66 |
| 3 | 60 | 82 | 3.0 | 4:1 | 110 |
| 4 | 62 | 83 | 3.0 | 4:1 | 83 |
| 5 | 67 | 87 | 3.0 | 4:1 | 112 |
| 6 | 67 | 93 | 3.0 | 4:1 | 107 |
| 7 | 62 | 105 | 3.0 | 4:1 | 103 |
| 8 | 62 | 139 | 3.0 | 4:1 | 43 |
| 9 | 66 | 225 | 3.0 | 4:1 | 47 |

FIG. 6 sets forth the GLC profile for the reaction product prior to distillation. The GLC profile is carried out on a SE-30 column programmed from 80° C. up to 220° C. at 8° C. per minute. The NMR, IR and mass spectrum for the reaction product are identical to those set forth on FIGS. 2-5, inclusive.

EXAMPLE III

Preparation of mixture containing ethyl ester of 1-methyl-5-norbornene-2-carboxylic acid and ethyl ester of 5-methylene norbornene-2-carboxylic acid Reaction:

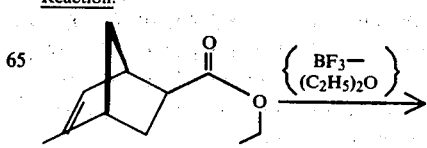

-continued

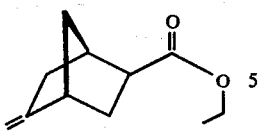

Boron trifluoride etharate (28 g) and 200 ml of toluene are charged into a 1 liter reaction flask equipped with a mechanical stirrer, condenser, thermomether and addition funnel. The solution is cooled to 5° C. and methylcyclopentadiene/ethyl acrylate adduct (275 g) is added dropwise, with the temperature maintained at 5°–10° C. with cooling. After the addition is complete, the reaction is quenched with 180 ml of ice water and the reaction mass is poured into a separatory funnel. The organic layer is washed once with 250 ml of 5% sodium hydroxide solution and twice with 250 ml of saturated sodium chloride solution. Solvent is removed under reduced pressure. The crude product is distilled on a 6"×½" vigreaux column to give 76 g (28% theoretical yield) of product; 40 g of which is odor approved.

The distillation fractions are as follows:

| Fraction No. | Vapor Temp. (°C.) | Liquid Temp. (°C.) | mm/Hg Pressure | Weight of Fraction (g.) |
|---|---|---|---|---|
| 1 | 43 | 76 | 1.0 | 8 |
| 2 | 44 | 76 | 1.0 | 7.9 |
| 3 | 42 | 75 | 0.8 | 5.9 |
| 4 | 42 | 75 | 0.8 | 4.1 |
| 5 | 43 | 78 | 0.8 | 5.4 |
| 6 | 40 | 82 | 0.8 | 5.3 |
| 7 | 43 | 82 | 0.8 | 5.8 |
| 8 | 45 | 92 | 0.8 | 6.8 |
| 9 | 45 | 102 | 0.8 | 7.9 |
| 10 | 44 | 115 | 0.8 | 4.6 |
| 11 | 89 | 142 | 0.8 | 6 |
| 12 | 89 | 146 | 0.8 | 3.6 |
| 13 | 83 | 150 | 0.8 | 4 |

FIG. 7 sets sets forth the GLC profile for the reaction product prior to distillation (conditions: SE-30 column programmed at 80° C.–220° C. at 8° C. per minute).

FIG. 8A represents the NMR spectrum for fraction 10 of the distillation product of the reaction product of Example III containing the compound having the structure:

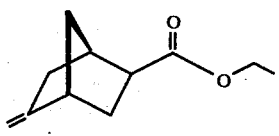

FIG. 8B represents the infrared spectrum for fraction 10 of the distillation product of the reaction product produced according to Example III containing the compound having the structure:

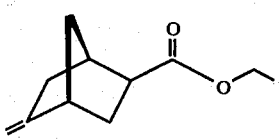

FIG. 9A represents the NMR spectrum for fraction 1 of the distillation product of the reaction product of Example III containing the compound having the structure:

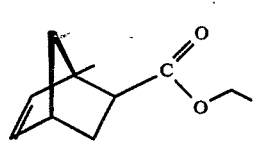

FIG. 9B represents the infrared spectrum for fraction 1 of the distillation product of the reaction product of Example III containing the compound having the structure:

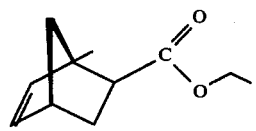

FIG. 10 represents the mass spectrum for the reaction product of Example III containing the compounds having the structures:

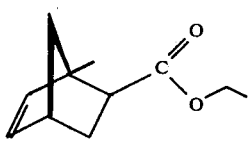

and

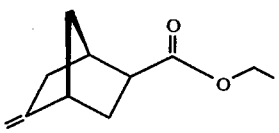

EXAMPLE IV

The following sweet, floral formula is produced:

| Ingredients | Parts by Weight |
|---|---|
| Hexyl Cinnamic Aldehyde | 12.0 |
| Benzyl Propionate | 8.0 |
| Isoeugenol | 2.0 |
| Indole - 10% in Diethyl Phthalate | 1.0 |
| Linalool | 8.0 |
| Benzyl Acetate | 8.0 |
| Vetivert Oil - Bourbon | 2.0 |
| Gamma Methyl Ionone | 1.0 |
| Phenyl Ethyl Alcohol | 6.0 |
| Patchouli Oil Light | 1.0 |
| Lavandin Abrialis | 4.0 |
| Hydroxy Citronellal | 4.0 |
| Bergamot Oil M.P.F. | 6.0 |
| Benzyl Salicylate | 13.0 |
| Musk Ambrette | 8.0 |
| Coumarin | 6.0 |
| Composition of matter produced according to Ex. III consisting of bulked fractions 4–10 and consisting of the compounds having the structures: | 10.0 |

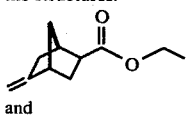

and

-continued

| Ingredients | Parts by Weight |
|---|---|
| 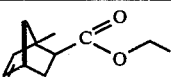 | |

At the 10% level in the foregoing sweet, floral formulation the compounds having the structures:

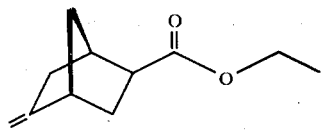

and

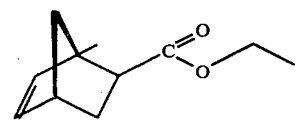

produced according to Example III contribute an intense sweet, fruity, green, herbaceous aroma with chamomile/calamnus type notes and this aroma is very long lasting.

EXAMPLE V

A stable lotion is prepared with the following formulations:

| Ingredients | Parts by Weight |
|---|---|
| poly (N,N-dimethyl-3,5-dimethylene piperidinium chloride) (Merquat 100, Merck & Co., U.S.A., average molecular weight 50,000-100,000, viscosity in 40% aqueous solution, 10,000 cps. | 1.0 |
| cocoamidopropyl dimethyl glycine (betaine) | 5.7 |
| myristyl dimethylamine oxide | 12.0 |
| stearic monoethanolamide opacifier | 2.0 |
| perfume as indicated in Table III (below) giving rise to the aroma profiles as indicated in Table III (below) | 0.5 |
| water, colour, salts, U.V. absorber | q.s. to 100 |

Two or three bottle capfuls of the above lotion held under the tap releasing the water into the bathtub yeilds a copiously foamed bubble bath with no visible precipitation flocculation, or "bathtub ring" even using hard water. Bathing in this bath is found to have a cleansing and pleasing emollient effect on the skin as described above.

When, after immersion in this bath, the body is soaped, rinsed and dried, an even better, more long-lasting emollient, moisturizing effect on the skin is observed. The foam or bubbles are substantially unaffected by the soaping step, and no precipitate, flocculate or "bathtub ring", or any bothersome film or coating on the bathtub surface is found.

The aroma produced is as is set forth in Table III below:

TABLE III

| Product | Aroma Profile |
|---|---|
| Product produced according to Example III, bulked fractions 4–10 consisting of the compounds having the structures: 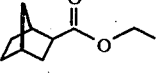 and 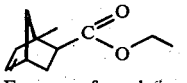 | A sweet, fruity, green, herbaceous aroma with chamomile and calamnus notes. |
| Fragrance formulation of Example IV | A sweet, floral aroma with very long lasting sweet, fruity, green, herbaceous chamomile and calamnus nuances. |

EXAMPLE VI

The following formulation is prepared with results in properties and use similar to those described in Example XI.

| Ingredients | Parts by Weight |
|---|---|
| "Merquat 100" | 1.0 |
| cocoamidopropyl dimethyl glycine | 8.0 |
| myristyl dimethyl amine oxide | 16.0 |
| Perfume ingredient as set forth in Table IV (below) giving rise to the aroma profiles as set forth in Table IV (below) | 0.8 |
| Water | q.s. to 100 |

The composition is a clear liquid. Its viscosity may be increased by addition of a lauric or myristic diethanolaminde or a soluble polyethylene glycol ester such as polyethylene glycol 6000. In addition, this composition may be rendered opaque by addition of stearic monoethanolamide stearate, polyethylene glycol 600 monostearate or a glyco amido stearate such as "Cerasynt 1P".

TABLE IV

| Product | Aroma Profile |
|---|---|
| Product produced according to Example III, bulked fractions 4–10 consisting of the compounds having the structures: 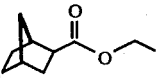 and 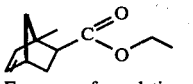 | A sweet, fruity, green, herbaceous aroma with chamomile and calamnus notes. |
| Fragrance formulation of Example IV | A sweet, floral aroma with very long lasting sweet, fruity, green, herbaceous chamomile and calamnus nuances. |

EXAMPLE VII

The following shampoo is prepared containing the following ingredients:

| Ingredients | Parts by Weight |
| --- | --- |
| Tridecyloxy polyethoxy ethanol of ten ethoxy groups | 17.3 |
| Polyoxyethylene (20) sorbitan monolaurate | 7.5 |
| Myristyl dimethylamine oxide (30% active) | 25.0 |
| $C_{10}$-$C_{20}$ fatty acyl monoethanolamide (cocomonoethanolamide) | 2.5 |
| Polyacrylamide of molecular weight of about 1,500,000 | 0.2 |
| Hydrogen peroxide (30% aqueous solution) | 0.5 |
| Perfume ingredient as indicated at Table V (below) giving rise to the aroma profiles as indicated in Table V (below) | 1.0 |
| Deionized water (3 micromhos/cm conductivity) | 46.0 |

A shampoo of the above composition is made in the following matter. First, the tridecyloxy polyethoxy ethanol is added to a clean mixing tank, with the agitator on, and the amine oxide, polyoxyethylene sorbitan monolaurate and cocomonoethanolamine are added sequentially, with continued agitaton. The mix is then heated to 68° C., until the cocomonoethanolamide is melted and/or dissolved. The hydrogen peroxide solution is then admixed with the mentioned nonionics and mixing is continued for about half an hour, in which the peroxide destroys any free amines or other harmful impurities that may be present. The mix is then cooled to 38° C.

In a separate mixer the polyacrylamide is gradually added to the formula weight of deionized water, with the mixer on. Addition is effected carefully and slowly (the polyacrylamide is sprinkled in) to avoid the production of "fish eyes" in the mix. After dissolving of the polyacrylamide the solution thereof is added to the first mixing tank with agitation and is blended with the nonionics, such mixings being at room temperature. Subsequently the perfume as indicated in Table V (below) giving rise to the aroma profile as set forth in Table V (below) is admixed with the balance of the composition and mixing is continued for another half hour.

TABLE V

| Product | Aroma Profile |
| --- | --- |
| Product produced according to Example III, bulked fractions 4–10 consisting of the compounds having the structures: 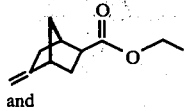 and 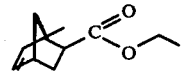 | A sweet, fruity, green, herbaceous aroma with chamomile and calamnus notes. |
| Fragrance formulation of Example IV | A sweet, floral aroma with very long lasting sweet, fruity, green, herbaceous chamomile and calamnus nuances. |

The product made is an excellent shampoo of satisfactory viscosity and aroma, foaming power, foam stability, low conductivity and good shampooing effects. The viscosity is about 1,000 centipoises at 20° C. and the conductivity, using the Hach Conductivity Meter, is 750 micromhos/cm. The foaming power is 250 ml and the foam stability is 22 seconds, by the test method previously described. In comparison, a commercial shampoo based on triethanolamine lauryl sulphate detergent has a conductivity of about 22,000 micromhos/cm, a viscosity of about 1,500 centipoises, a foaming power of about 380 ml and a foam stability of 60 seconds.

In panel evaluations of the experimental shampoo compared to a different commercial product, in actual shampooing, the experimental formula was adjudged significantly better in being less drying, porducing a softer feel for the wet hair, leaving the wet hair easier to comb, being less prone to accumulate static charges (less flyaway) and having a foam of better appearance and feel. Additionally, the experimental product was judged better in almost all hair effect properties, with the control only being about equal to it in curl retention. In properties other than those mentioned the experimental product was better in rinsability, the control was better in foam build-up rate and the foams were about equal in volume and stability.

In the shampooing described herein and in subsequent Examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE VIII

Fabric Freshener Composition

A fabric freshener composition is prepared as follows:

| Ingredients | Parts by Weight |
| --- | --- |
| Sodium bicarbonate | 3 |
| "Kyro" EOB (Trade Mark)* | 1 |
| Perfume ingredient as set forth in Table VI below giving rise to an aroma as set forth in Table VI below | 1 |
| Water | 0.05 |

The composition of this Example is prepared by simply mixing the ingredients.

The above described composition is applied to a lightly soiled and wrinkled fabric as droplets (ca. 5.0 mm avg. size) using a trigger acton sprayer having a nozzle which is adjustable to provide composition droplets in the desired range. The composition is applied at a rate of about 1 gram of composition to about 10 grams of fabric.

The fabric is then placed in an automatic dryer and dried, with tumbling action, at a temperature of 60° C.–80° C. for a period of 15 minutes. The fabric is rendered free of wrinkles and static, and has a fresh appearance and pleasant odor profile as set forth in Table VI below. Surprisingly, the sodium bicarbonate is not visible on the refreshed fabric.

In the foregoing procedure, substantially the same results were obtained when sodium carbonate is substituted for the sodium bicarbonate.

TABLE VI

| Product | Aroma Profile |
|---|---|
| Product produced according to Example III, bulked fractions 4–10 consisting of the compounds having the structures: 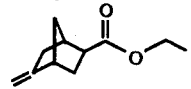 and 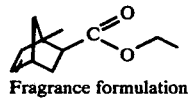 | A sweet, fruity, green, herbaceous aroma with chamomile and calamnus notes. |
| Fragrance formulation of Example IV | A sweet, floral aroma with very long lasting sweet, fruity, green, herbaceous chamomile and calamnus nuances. |

EXAMPLE IX

Perfumed Liquid Detergent

Concentrated liquid detergents (lysine salts of n-dodecyl benzene sulfonic acid as more specifically described in U.S. Pat. No. 3,948,818, issued on Apr. 6, 1976) with aromas as indicated in Table VII below are prepared containing 0.10%, 0.15%, 0.20%, 0.25%, 0.30%, 0.40%, 0.50% and 0.80% of the perfume ingredient as set forth in Table VII below. The detergenets are prepared by adding a homogeneously mixing the appropriate quantity of perfume ingredient as set forth in Table VII below. The detergents all possess aromas as set forth in Table VII below with the intensity of each increasing with greater concentrations of the perfume ingredient as indicated in Table VII below.

TABLE VII

| Product | Aroma Profile |
|---|---|
| Product produced according to Example III, bulked fractions 4–10 consisting of the compounds having the structures: 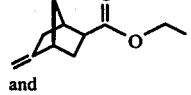 and 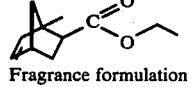 | A sweet, fruity, green, herbaceous aroma with chamomile and calamnus notes. |
| Fragrance formulation of Example IV | A sweet, floral aroma with very long lasting sweet, fruity, green, herbaceous chamomile and calamnus nuances. |

EXAMPLE X

Preparation of a Cologne and Handkerchief Perfume

The perfume ingredient as set forth in Table VIII below is incorporated into colognes at concentrations of 2.0%, 2.5%, 3.0%, 3.5%, 4.0%, 5.0% and 6.0% in 75%, 80%, 85%, 90% and 95% aqueous ethanol solutions. Distinct and definite aromas as set forth in Table VIII below are imparted to the colognes. The perfume ingredients as indicated in Table VIII below are also added to handkerchief perfumes at concentrations of 15%, 20%, 25%, 30% and 35% (in 75%, 80%, 85%, 90% and 95% aqueous ethanol) and aroma profiles as set forth in Table VIII are imparted to the handkerchief perfume.

TABLE VIII

| Product | Aroma Profile |
|---|---|
| Product produced according to Example III, bulked fractions 4–10 consisting of the compounds having the structures: 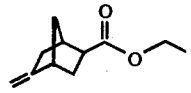 and 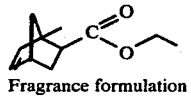 | A sweet, fruity, green, herbaceous aroma with chamomile and calamnus notes. |
| Fragrance formulation of Example IV | A sweet, floral aroma with very long lasting sweet, fruity, green, herbaceous chamomile and calamnus nuances. |

EXAMPLE XI

The following concentrate is prepared:

| Ingredient | Percent |
|---|---|
| Geraniol | 1.00 |
| Ethyl methyl phenyl glycidate | 3.33 |
| Bulked fractions 4–10 prepared according to Example III containing the compounds having the structures: 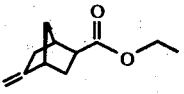 and 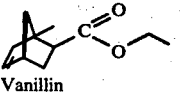 | |
| Vanillin | 5.66 |
| Ethyl pelargonate | 13.06 |
| Isoamyl acetate | 14.00 |
| Ethyl butyrate | 58.18 |

EXAMPLE XII

Another concentrate is prepared as follows:

| Ingredient | Percent |
|---|---|
| Naphthyl ethyl ether | 0.96 |
| Vanillin | 2.66 |
| Ethyl methyl phenyl glycidate | 2.88 |
| Bulked fractions 4–10 prepared according to Example III containing the compounds having the structures: 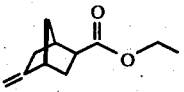 and 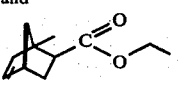 | 4.90 |
| Ethyl acetate | 9.58 |
| Isoamyl acetate | 12.25 |
| Ethyl butyrate | 26.20 |
| Isoamyl butyrate | 40.57 |

EXAMPLE XIII

The concentrate prepared in Example XI is dissolved in 4 volumes of propylene and the mixture is added to a hard candy melt at the rate of 1.5 oz. of the concentrate solution per 100 lbs. of melt. After the finished candy has been produced, it is found to have an excellent strawberry flavor. When the candy is compared with candy made under the same conditions, but without the mixture of compounds having the structures:

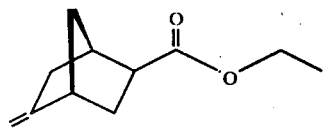

and

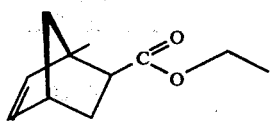

prepared according to the process of Example III in the concentrate, it is found to have an inferior strawberry flavor.

EXAMPLE XIV

The propylene glycol solution of the concentrate as prepared in Example XIII is added to a simple syrup at the rate of ⅛ oz. per gallon of syrup. The syrup is acidified by the addition of 1.5 oz. of 50% aqueous citric acid solution to each gallon of syrup. A carbonated beverage is prepared by admixing one oz. of the flavored acidified syrup with 5 oz. of carbonated water. The beverage so prepared has an excellent fresh strawberry flavor, and is found to be markedly superior to a beverage prepared in the same manner but without the mixture of compounds having the structures:

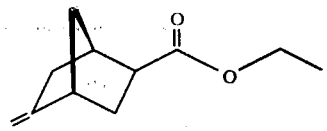

and

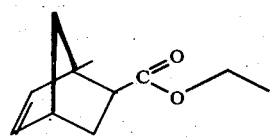

prepared according to the process of Example III in the concentrate.

EXAMPLE XV

The flavor concentrate prepared in XII is admixed with gum arabic and in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor and is markedly superior to a gelatin dessert prepared in the same maner without the mixture of compounds having the structures:

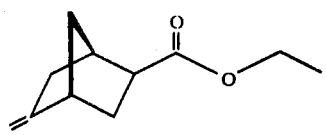

and

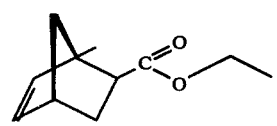

prepared according to the process of Example III in the concentrate.

EXAMPLE XVI

Fruited Tapioca Cream

The contents of Ann Page Tapioca pudding mix (ingredients: sugar, corn starch, tapioca, sodium chloride, tapioca flavor and artificial color; Net weight 138 grams) is emptied into a sauce pan. Three cups of milk are added together with one beaten egg yolk previously blended therewith. The resulting mix is cooked over medium heat stirring constantly while slowly adding at the rate of 0.2%, either one of the flavor materials of Example III containing the compounds having the structures:

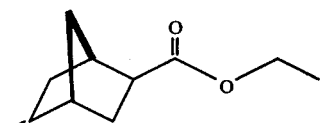

and

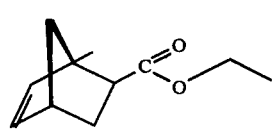

The resulting mixture after heating, is then cooled to room temperature in the saucepan. One egg white is slowly added to the resulting mixture together with three tablespoon of sugar. The resulting mixture is then blended and chilled yielding a tropical fruit flavor with a mango nuance.

EXAMPLE XVII

Tobacco Formulation

A tobacco mixture is produced by admixing the following materials:

| Ingredients | Parts by Weight |
| --- | --- |
| Bright Tobacco | 40.1 |
| Burley Tobacco | 24.9 |
| Maryland Tobacco | 1.1 |
| Turkish Tobacco | 11.6 |
| Stem (flue-cured) (Tobacco) | 14.2 |
| Glycerine | 2.8 |

-continued

| Ingredients | Parts by Weight |
|---|---|
| Water | 5.3 |

The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.5% to the above tobacco formulation, with half of the tobacco then treated with 5 and 10 ppm of the mixture of compounds having the structures:

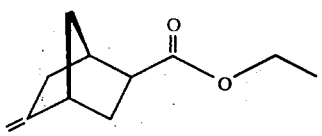

and

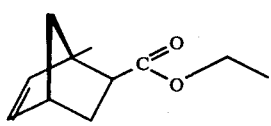

produced according to the process of Example III (bulked fractions 4–10). The control cigaretts produced from tobacco formulation not containing the mixture of compounds having the structures:

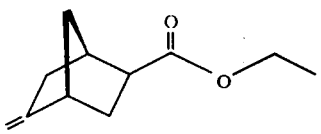

and

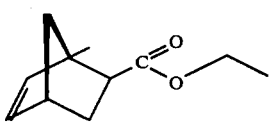

produced according to the process of Example III (bulked fractions 4–10) and the experimental cigarettes with tobacco containing the mixture of compounds having the structures:

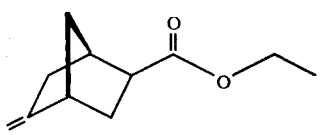

and

produced according to the process of Example III (bulked fractions 4–10) are evaluated by paired comparison and the results are as follows:

The cigarettes of the mixtures of compounds having the structures:

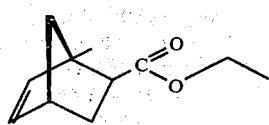

and

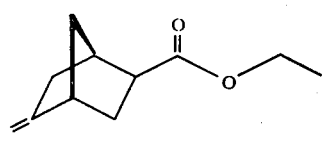

produced according to the process of Example III (bulked fractions 4–10) are found to be, on smoking, more aromatic, and richer in aroma, i.e., having a well pronounced, pleasant, full aroma than the control cigarettes.

In the smoke, the cigarettes of the mixture of compounds having the structures:

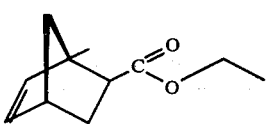

and

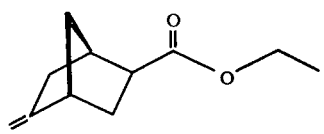

produced according to the process of Example III (bulked fractions 4–10) are found to be more aromatic, sweeter, more bitter, less harsh in the mouth and throat and slightly woody and smokey by comparison to the control. All cigarettes are evaluated for smoke flavor with a 20 mm cellulose acetate filter.

The mixture of compounds having the structures:

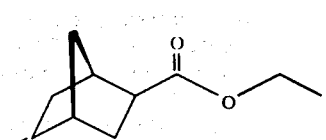

and

-continued

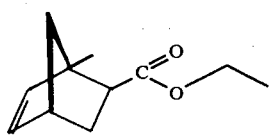

produced according to the process of Example III (bulked fractions 4–10) enhances the tobacco-like taste and aroma of the blended cigarette and gives the cigarette a Turkish-like character.

What is claimed is:

1. At least one compound defined according to the structure:

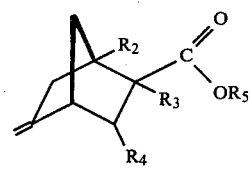

wherein $R_2$ is hydrogen and $R_3$ and $R_4$ represent hydrogen or methyl; and wherein $R_5$ is $C_1$–$C_4$ lower alkyl.

2. The process for preparing a compound defined according to claim 1 comprising rearranging a norbornane derivative according to the reaction step:

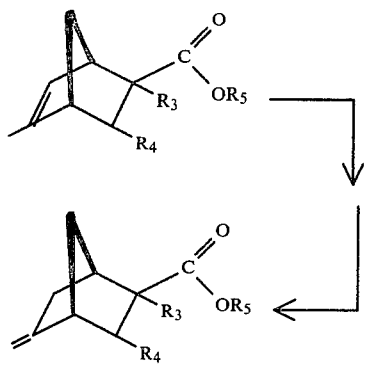

using a rearrangement agent;
wherein $R_3$ and $R_4$ each represent hydrogen or methyl and wherein $R_5$ is $C_1$–$C_4$ lower alkyl at a temperature in the range of from about 0° C. up to about 15° C. in the presence of an inert solvent.

3. The process of claim 2 wherein the rearrangement agent is boron trifluoride diethyl ether complex and the reaction is carried out in the presence of a solvent selected from the group consisting of toluene and xylene.

* * * * *